US012758593B2

(12) United States Patent
Altier

(10) Patent No.: US 12,758,593 B2
(45) Date of Patent: Oct. 13, 2026

(54) **RECOMBINANT BACTERIA PRODUCING CHEMICALS INHIBITORY TO *Salmonella* INVASION**

(71) Applicant: CORNELL UNIVERSITY, Ithaca, NY (US)

(72) Inventor: Craig Altier, Freeville, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 731 days.

(21) Appl. No.: 17/915,780

(22) PCT Filed: Mar. 31, 2021

(86) PCT No.: PCT/US2021/025037
§ 371 (c)(1),
(2) Date: Sep. 29, 2022

(87) PCT Pub. No.: WO2021/202630
PCT Pub. Date: Oct. 7, 2021

(65) Prior Publication Data

US 2023/0201275 A1 Jun. 29, 2023

Related U.S. Application Data

(60) Provisional application No. 63/003,525, filed on Apr. 1, 2020.

(51) Int. Cl.

| | |
|---|---|
| ***A61K 35/741*** | (2015.01) |
| ***A23K 10/16*** | (2016.01) |
| ***A61K 35/744*** | (2015.01) |
| ***A61K 35/745*** | (2015.01) |
| ***A61K 35/747*** | (2015.01) |
| ***A61P 31/04*** | (2006.01) |
| ***C07K 14/195*** | (2006.01) |
| ***C12N 15/52*** | (2006.01) |
| ***C12N 15/74*** | (2006.01) |

(52) U.S. Cl.
CPC ............ *A61K 35/741* (2013.01); *A23K 10/16* (2016.05); *A61P 31/04* (2018.01); *C07K 14/195* (2013.01); *C12N 15/52* (2013.01); *C12N 15/74* (2013.01)

(58) Field of Classification Search
CPC .. A61K 35/741; A61K 35/744; A61K 35/745; A61K 35/747; A23K 10/16; A23K 50/10; A23K 50/20; A23K 50/30; A23K 50/75; A23K 20/158; A23K 10/18; A61P 31/04; C07K 14/195; C12N 15/52; C12N 15/74; C12N 1/20; C12N 9/88; C12R 2001/19; C12Y 402/01017; A23V 2002/00; Y02A 50/30; A23L 33/135; C12P 7/6409
See application file for complete search history.

(56) References Cited

U.S. PATENT DOCUMENTS

2009/0227028 A1 9/2009 Newman et al.

FOREIGN PATENT DOCUMENTS

WO WO 2011142724 A1 * 11/2011 ............. C07C 57/03

OTHER PUBLICATIONS

Beaulieu E.D. et al., "Characterization of a Diffusible Signaling Factor from Xylella Fastidiosa", mBio 4(1): 00539-12 (Jan./Feb. 2013).
Tscherner M. et al., "A Synthetic System That Senses Candida Albicans and Inhibits Virulence Factors", ACS Synthetic Biology 8:434-444 (Feb. 15, 2019).
GenBank Accession No. AE009442.1 (2 pages) (Aug. 20, 2021).
International Search Report and Written Opinion dated Sep. 27, 2021 received in International Application No. PCT/US2021/025037.
Kandel P.P., "Xylella Fastidiosa Strain WM1-1 Hybrid Sensor Histidine Kinase/Response Regulator Gene, Partial CDS; Enoyl-CoA Hydratase Gene, Complete CDS; and Aspartate Kinase Gene, Partial CDS", retrieved from EBI Accession No. EM_STD:KY616735 (May 12, 2017) (cited in Extended Supp EP Search Report).
Extended Supplementary European Search Report dated Mar. 27, 2025 received in European Application No. 21 78 1809.5.
Liu H. et al., "Comparative Analysis of Biofilm Characterization of Probiotic *Escherichia coli*", Front. Microbiol. 15:1365562 (2024).

* cited by examiner

*Primary Examiner* — Satyendra K Singh
(74) *Attorney, Agent, or Firm* — Scully, Scott, Murphy & Presser, P.C.

(57) ABSTRACT

The present disclosure is directed to genetically modified bacteria that produce a diffusible signal factor (DSF). The disclosure also provides methods for treating or preventing *Salmonella* infection/invasion in a subject. The disclosure further provides vectors and compositions for carrying out the methods disclosed herein.

27 Claims, 13 Drawing Sheets

Specification includes a Sequence Listing.

*cis*-11-methy-dodecenoic acid (DSF)

*cis*-2-dodecenoic acid (BDSF)

*cis,cis*-11-methyldodeca-2,5-dienoic acid (CDSF)

*cis*-10-methyl-2-dodecenoic acid (IDSF/DSF-II)

13-methyltetradecanoic acid (*Le*DSF3)

*cis*-2-tetradecenoic acid (*Xf*DSF1)

Trans-2-decenoic acid (SDSF)

*cis*-2-decenoic acid

2-*cis*-hexadecenoic acid (XfDSF2)

cis-9-methyl-2-decenoic acid cis-2-undecenoic acid

3(*R*)-hydroxyacyl-ACP

*cis*-2-acyl-ACP

SEQUENCE LISTING

```
<160> NUMBER OF SEQ ID NOS: 24

<210> SEQ ID NO 1
<211> LENGTH: 290
<212> TYPE: PRT
<213> ORGANISM: Xylella fastidiosa Temecula1

<400> SEQUENCE: 1

Met Ser Ala Val His Pro Ile Pro His Pro Ile Cys Glu Ser Ser Ile
1               5                   10                  15

Arg Ile Ile Glu Glu Thr His Arg Asn Val Tyr Trp Ile Tyr Met His
            20                  25                  30

Ala His Leu Ala Arg Thr Thr Gly Ala Ala Tyr Phe Ser Leu Lys Leu
        35                  40                  45

Ile Asp Asp Ile Met Asn Tyr Gln Ser Val Leu Arg Gln Arg Leu Lys
    50                  55                  60

Glu Gln Thr Val Gln Leu Pro Phe Val Val Leu Ala Ser Asp Ser Asn
65                  70                  75                  80

Val Phe Asn Leu Gly Gly Asp Leu Gln Leu Phe Cys Asp Leu Ile Arg
                85                  90                  95

Arg Lys Glu Arg Glu Ala Leu Leu Asp Tyr Ala Cys Arg Cys Val Arg
            100                 105                 110

Gly Ala Tyr Ala Phe His Ala Gly Leu Asn Ala Asn Val His Ser Ile
        115                 120                 125

Ala Leu Leu Gln Gly Asn Ala Leu Gly Gly Gly Phe Glu Ala Ala Leu
    130                 135                 140

Cys Cys His Thr Ile Val Ala Glu Glu Gly Val Met Met Gly Phe Pro
145                 150                 155                 160

Glu Val Leu Phe Asp Leu Phe Pro Gly Met Gly Ala Tyr Ser Phe Met
                165                 170                 175

Arg Gln Arg Ile Ser Pro Lys Leu Ala Glu Arg Leu Ile Leu Glu Gly
            180                 185                 190

Asn Leu Tyr Ser Ser Glu Glu Leu Leu Ala Ile Gly Leu Ile Asp Lys
        195                 200                 205

Val Val Pro Arg Gly Lys Gly Ile Glu Ala Val Glu Gln Ile Ile Arg
    210                 215                 220

Asp Ser Lys Arg Arg Gln Tyr Thr Trp Ala Ala Met Gln Glu Val Lys
225                 230                 235                 240

Lys Ile Ala His Glu Val Ser Leu Glu Glu Met Ile Arg Ile Thr Glu
                245                 250                 255

Leu Trp Val Asp Ser Ala Leu Lys Leu Ser Asn Lys Ser Leu Arg Thr
            260                 265                 270

Met Glu Arg Leu Ile Arg Ala Gln Gln Thr His Lys Asn Thr Ala Leu
        275                 280                 285
```

-continued

Lys Asn
290

<210> SEQ ID NO 2
<211> LENGTH: 873
<212> TYPE: DNA
<213> ORGANISM: Xylella fastidiosa Temecula1

<400> SEQUENCE: 2
atgtccgctg tacatcccat tcctcacccc atatgcgaat catccattcg catcatcgaa 60
gaaacccatc gcaatgtgta ctggatctat atgcatgctc atctcgccag aaccacggga 120
gccgcctatt tttccttaaa actgattgat gacatcatga attatcaatc cgtacttaga 180
caacgtttaa aggaacaaac ggttcaatta ccattcgttg ttctcgcctc ggacagcaat 240
gtatttaatt taggcgggga tctgcagctt ttttgtgacc tgatacgccg taaggagcgt 300
gaagcattat tggactatgc ctgccgctgt gtgcgtggag cctatgcgtt ccatgctggg 360
ctcaatgcta atgtgcatag catcgcgctg ctccaaggca atgcgcttgg aggaggcttc 420
gaagctgcgc tctgttgcca taccatcgta gctgaagaag gtgtgatgat gggttttcct 480
gaagtattgt tcgatctttt cccaggcatg ggagcctact ctttcatgcg tcaacgcatc 540
tctcctaaac tggccgaacg cctcatcctt gagggcaatc tctacagttc cgaagaatta 600
ttggcgattg ggctgatcga caaagtagta ccgcgcggca aggggataga agcagtcgag 660
caaatcatcc gtgacagcaa acgccgtcaa tatacttggg cagccatgca ggaggtgaaa 720
aaaatcgcac acgaagtctc tttagaagaa atgatacgca tcaccgaact ctgggtagac 780
agtgcattga aactaagtaa caaatcactc cgaactatgg agcgcctgat ccgcgcccag 840
cagactcaca aaaacacagc actaaaaaac tga 873

<210> SEQ ID NO 3
<211> LENGTH: 947
<212> TYPE: DNA
<213> ORGANISM: Artificial Sequence
<220> FEATURE:
<223> OTHER INFORMATION: Oligonucleotide

<400> SEQUENCE: 3
gagctgttga caattaatca tcggctcgta taatgtgtgc attgtgagcg gaataaagga 60
ggacagctat gagtgccgtt catccgatcc ctcatccaat ttgcgagtca tccatccgta 120
ttattgaaga aacacaccgc aacgtctact ggatttacat gcacgcgcat ttggcccgta 180
ccactggagc tgcatacttt agccttaaac tgatcgatga catcatgaac tatcagtccg 240
tgcttcgtca gcgtcttaaa gagcaaacgg tccaattgcc gtttgtagtc ttagcctccg 300
atagcaatgt tttcaacctg gggggcgatc ttcagttatt ttgcgatctt attcgtcgta 360
aagagcgcga agcattactg gactacgcgt gccgttgtgt gcgtggggcc tatgctttcc 420
acgcaggatt gaacgcaaac gtgcacagca tcgccttatt acagggaaat gcgcttggtg 480
gcggttttga ggctgcctta tgctgtcaca caatcgttgc cgaagagggg gtaatgatgg 540
ggtttccgga agtgttgttt gatttgttcc ctggtatggg tgcatattca ttcatgcgcc 600
agcgcatttc gcctaaactg gcggaacgtt tgatccttga gggtaatctg tacagttcag 660
aagagttgct ggcgattggt cttatcgata aagtggttcc ccgtgggaag gggattgaag 720
cagtggaaca aattatccgc gactccaagc gccgtcagta tacctgggca gcgatgcaag 780
aggtgaaaaa aatcgcccat gaagtaagtc tggaagagat gatccgcatc actgagttgt 840

-continued gggtagattc ggctttgaaa ctgtccaata aatctcttcg cacgatggag cgcttaatcc 900
gcgcccaaca gactcacaag aatacggctt tgaagaactg aagatct 947

<210> SEQ ID NO 4
<211> LENGTH: 961
<212> TYPE: DNA
<213> ORGANISM: Artificial Sequence
<220> FEATURE:
<223> OTHER INFORMATION: Oligonucleotide

<400> SEQUENCE: 4
gagctgttga caattaatca tcggctcgta taatgtgtgg aattgtgagc ggataacaat 60
ttcacacagg aaacagaatt ctatgtctgc ggttcacccg atcccgcacc cgatctgcga 120
atcttctatc cgtatcatcg aagaaaccca ccgtaacgtt tactggatct acatgcacgc 180
gcacctggcg cgtaccaccg gtgcggcgta cttctctctg aaactgatcg acgacatcat 240
gaactaccag tctgttctgc gtcagcgtct gaaagaacag accgttcagc tgccgttcgt 300
tgttctggcg tctgactcta acgttttcaa cctgggtggt gacctgcagc tgttctgcga 360
cctgatccgt cgtaaagaac gtgaagcgct gctggactac gcgtgccgtt gcgttcgtgg 420
tgcgtacgcg ttccacgcgg gtctgaacgc gaacgttcac tctatcgcgc tgctgcaggg 480
taacgcgctg ggtggtggtt tcgaagcggc gctgtgctgc cacaccatcg ttgcggaaga 540
aggtgttatg atgggtttcc cggaagttct gttcgacctg ttcccgggta tgggtgcgta 600
ctctttcatg cgtcagcgta tctctccgaa actggcggaa cgtctgatcc tggaaggtaa 660
cctgtactct tctgaagaac tgctggcgat cggtctgatc gacaaagttg ttccgcgtgg 720
taaaggtatc gaagcggttg aacagatcat ccgtgactct aaacgtcgtc agtacacctg 780
ggcggcgatg caggaagtta aaaaaatcgc gcacgaagtt tctctggaag aaatgatccg 840
tatcaccgaa ctgtgggttg actctgcgct gaaactgtct aacaaatctc tgcgtaccat 900
ggaacgtctg atccgtgcgc agcagaccca caaaaacacc gcgctgaaaa actgaagatc 960
t 961

<210> SEQ ID NO 5
<211> LENGTH: 874
<212> TYPE: DNA
<213> ORGANISM: Artificial Sequence
<220> FEATURE:
<223> OTHER INFORMATION: Oligonucleotide

<400> SEQUENCE: 5
atgtctgcgg ttcacccgat cccgcacccg atctgcgaat cttctatccg tatcatcgaa 60
gaaacccacc gtaacgttta ctggatctac atgcacgcgc acctggcgcg taccaccggt 120
gcggcgtact tctctctgaa actgatcgac gacatcatga actaccagtc tgttctgcgt 180
cagcgtctga aagaacagac cgttcagctg ccgttcgttg ttctggcgtc tgactctaac 240
gttttcaacc tgggtggtga cctgcagctg ttctgcgacc tgatccgtcg taaagaacgt 300
gaagcgctgc tggactacgc gtgccgttgc gttcgtggtg cgtacgcgtt ccacgcgggt 360
ctgaacgcga acgttcactc tatcgcgctg ctgcagggta acgcgctggg tggtggtttc 420
gaagcggcgc tgtgctgcca caccatcgtt gcggaagaag gtgttatgat gggtttcccg 480
gaagttctgt tcgacctgtt cccgggtatg ggtgcgtact ctttcatgcg tcagcgtatc 540
tctccgaaac tggcggaacg tctgatcctg gaaggtaacc tgtactcttc tgaagaactg 600
ctggcgatcg gtctgatcga caaagttgtt ccgcgtggta aaggtatcga agcggttgaa 660

```
cagatcatcc gtgactctaa acgtcgtcag tacacctggg cggcgatgca ggaagttaaa    720

aaaatcgcgc acgaagtttc tctggaagaa atgatccgta tcaccgaact gtgggttgac    780

tctgcgctga aactgtctaa caaatctctg cgtaccatgg aacgtctgat ccgtgcgcag    840

cagacccaca aaaacaccgc gctgaaaaac tgaa                                874
```

<210> SEQ ID NO 6
<211> LENGTH: 870
<212> TYPE: DNA
<213> ORGANISM: Cronobacter turicensis

<400> SEQUENCE: 6

```
atgtcagtat tcaaccaatc gacctgcaaa ctctttaccg atacagcgcg ttttactcag     60

ctttccggct tttacgagga agaacgccgc attatctgga tgatgttgcg ggctcagccg    120

cgtccgtgtt ttaaccatgt ccttatcgaa gagataatga acctcagcta tctggtgcag    180

gaggccagac tggaggtgga tttctgggtc accggctcgc tggttcccgg catgtataac    240

accggcggcg atttgcagtt tttcgtcgac tgcattcgca acggcaaacg tgaagcgcta    300

cgcgcctatg cgcgcgcctg cgtggactgc gtacacgccg cctcgcgcgg gtttgactgc    360

ggcgccatta gccttgcgat ggtagaaggc agcgcgctcg gcggcggttt cgaggcggcg    420

ctggcgcacc attttgtgct ggcccagcgt gacgcccgca tggggttccc ggagattgcc    480

tttaatctct tccccggcat gggcggctat tcgctggtga caaggcgcgc cggaatgcgc    540

cttgccgagg agctcatctg gcagggcgaa tcgcacaccg ccgagtggta tcagccgcag    600

gggctggtgg atcagctctt tgagccaggc cagggatttg tggcgacacg gacgttcatc    660

gataccctga aaccgcgtct gaacggggtg agggcgatgc ttcgcgcgcg ccagcgcgtg    720

ctgcggcttt cgcgtaatga gctgatggaa atcaccgaag actgggtaga tgcggcgttc    780

agcctggagc cgaaagatgt gggctacatg gaacgtctga tccagctgca aaaccgccat    840

accgccgcgg ccctgcgtaa agcaggctaa                                     870
```

<210> SEQ ID NO 7
<211> LENGTH: 289
<212> TYPE: PRT
<213> ORGANISM: Cronobacter turicensis

<400> SEQUENCE: 7

```
Met Ser Val Phe Asn Gln Ser Thr Cys Lys Leu Phe Thr Asp Thr Ala
1               5                   10                  15

Arg Phe Thr Gln Leu Ser Gly Phe Tyr Glu Glu Glu Arg Arg Ile Ile
            20                  25                  30

Trp Met Met Leu Arg Ala Gln Pro Arg Pro Cys Phe Asn His Val Leu
        35                  40                  45

Ile Glu Glu Ile Met Asn Leu Ser Tyr Leu Val Gln Glu Ala Arg Leu
    50                  55                  60

Glu Val Asp Phe Trp Val Thr Gly Ser Leu Val Pro Gly Met Tyr Asn
65                  70                  75                  80

Thr Gly Gly Asp Leu Gln Phe Phe Val Asp Cys Ile Arg Asn Gly Lys
                85                  90                  95

Arg Glu Ala Leu Arg Ala Tyr Ala Arg Ala Cys Val Asp Cys Val His
            100                 105                 110

Ala Ala Ser Arg Gly Phe Asp Cys Gly Ala Ile Ser Leu Ala Met Val
        115                 120                 125
```

-continued

```
Glu Gly Ser Ala Leu Gly Gly Gly Phe Glu Ala Ala Leu Ala His His
    130                 135                 140

Phe Val Leu Ala Gln Arg Asp Ala Arg Met Gly Phe Pro Glu Ile Ala
145                 150                 155                 160

Phe Asn Leu Phe Pro Gly Met Gly Gly Tyr Ser Leu Val Thr Arg Arg
                165                 170                 175

Ala Gly Met Arg Leu Ala Glu Glu Leu Ile Trp Gln Gly Glu Ser His
            180                 185                 190

Thr Ala Glu Trp Tyr Gln Pro Gln Gly Leu Val Asp Gln Leu Phe Glu
        195                 200                 205

Pro Gly Gln Gly Phe Val Ala Thr Arg Thr Phe Ile Asp Thr Leu Lys
    210                 215                 220

Pro Arg Leu Asn Gly Val Arg Ala Met Leu Arg Ala Arg Gln Arg Val
225                 230                 235                 240

Leu Arg Leu Ser Arg Asn Glu Leu Met Glu Ile Thr Glu Asp Trp Val
                245                 250                 255

Asp Ala Ala Phe Ser Leu Glu Pro Lys Asp Val Gly Tyr Met Glu Arg
            260                 265                 270

Leu Ile Gln Leu Gln Asn Arg His Thr Ala Ala Ala Leu Arg Lys Ala
        275                 280                 285

Gly
```

<210> SEQ ID NO 8
<211> LENGTH: 870
<212> TYPE: DNA
<213> ORGANISM: Xanthomonas campestris pv. campestris

<400> SEQUENCE: 8

```
atgtctgcag ttcaaccctt cattcgtacc aatattggct cgaccctacg catcatcgaa      60

gaaccgcagc gtgacgttta ctggatccat atgcatgccg acctggccat caatcccggg     120

cgggcctgtt tctcgacacg cctggtcgac gacatcactg gctaccagac caacctggga     180

caacgcttga atactgccgg tgtgctggcg ccgcacgtgg tgctggcatc ggacagcgac     240

gtgttcaatc tgggcggtga tctggccctg ttctgccaac tgatccgcga aggcgaccgc     300

gcccgccttc tcgactacgc ccaacgctgc gtgcgcggcg tgcatgcctt tcatgtcggc     360

ctgggcgcgc gtgcgcacag cattgcgctg gtccagggca atgcgcttgg cggcgggttc     420

gaagcggcac taagctgcca cacgatcatt gccgaggaag gcgtgatgat ggggctgccc     480

gaagtgctgt tcgacctatt tccggggatg ggcgcctact ccttcatgtg ccagcgcatc     540

agtgcgcacc tggcgcaaaa gatcatgctt gaaggcaacc tgtattcggc cgaacagctg     600

ctcggcatgg gcctggtcga ccgtgtggta ccgcgtggcc agggcgtggc cgcagtggaa     660

caggtgatcc gcgagagcaa gcgcacgcca cacgcgtggg cggcgatgca acaagtgcgc     720

gaaatgacca ccgccgtgcc gcttgaggag atgatgcgca tcaccgaaat ctgggtagat     780

accgccatgc aactcggcga aaaatcactg cgtaccatgg accgcctggt gcgcgcgcag     840

tcgcgtcgct cagggctcga cgcgggctga                                      870
```

<210> SEQ ID NO 9
<211> LENGTH: 870
<212> TYPE: DNA
<213> ORGANISM: Artificial Sequence
<220> FEATURE:
<223> OTHER INFORMATION: Oligonucleotide

<400> SEQUENCE: 9

```
atgtctgcgg ttcagccgtt catccgtacc aacatcggtt ctaccctgcg tatcatcgaa     60

gaaccgcagc gtgacgttta ctggatccac atgcacgcgg acctggcgat caacccgggt    120

cgtgcgtgct tctctacccg tctggttgac gacatcaccg gttaccagac caacctgggt    180

cagcgtctga acaccgcggg tgttctggcg ccgcacgttg ttctggcgtc tgactctgac    240

gttttcaacc tgggtggtga cctggcgctg ttctgccagc tgatccgtga aggtgaccgt    300

gcgcgtctgc tggactacgc gcagcgttgc gttcgtggtg ttcacgcgtt ccacgttggt    360

ctgggtgcgc gtgcgcactc tatcgcgctg gttcagggta acgcgctggg tggtggtttc    420

gaagcggcgc tgtcttgcca caccatcatc gcggaagaag gtgttatgat gggtctgccg    480

gaagttctgt tcgacctgtt cccgggtatg ggtgcgtact ctttcatgtg ccagcgtatc    540

tctgcgcacc tggcgcagaa aatcatgctg gaaggtaacc tgtactctgc ggaacagctg    600

ctgggtatgg gtctggttga ccgtgttgtt ccgcgtggtc agggtgttgc ggcggttgaa    660

caggttatcc gtgaatctaa acgtaccccg cacgcgtggg cggcgatgca gcaggttcgt    720

gaaatgacca ccgcggttcc gctggaagaa atgatgcgta tcaccgaaat ctgggttgac    780

accgcgatgc agctgggtga aaaatctctg cgtaccatgg accgtctggt tcgtgcgcag    840

tctcgtcgtt ctggtctgga cgcgggttga                                     870
```

```
<210> SEQ ID NO 10
<211> LENGTH: 289
<212> TYPE: PRT
<213> ORGANISM: Xanthomonas campestris pv. campestris

<400> SEQUENCE: 10

Met Ser Ala Val Gln Pro Phe Ile Arg Thr Asn Ile Gly Ser Thr Leu
1               5                   10                  15

Arg Ile Ile Glu Glu Pro Gln Arg Asp Val Tyr Trp Ile His Met His
            20                  25                  30

Ala Asp Leu Ala Ile Asn Pro Gly Arg Ala Cys Phe Ser Thr Arg Leu
        35                  40                  45

Val Asp Asp Ile Thr Gly Tyr Gln Thr Asn Leu Gly Gln Arg Leu Asn
    50                  55                  60

Thr Ala Gly Val Leu Ala Pro His Val Val Leu Ala Ser Asp Ser Asp
65                  70                  75                  80

Val Phe Asn Leu Gly Gly Asp Leu Ala Leu Phe Cys Gln Leu Ile Arg
                85                  90                  95

Glu Gly Asp Arg Ala Arg Leu Leu Asp Tyr Ala Gln Arg Cys Val Arg
            100                 105                 110

Gly Val His Ala Phe His Val Gly Leu Gly Ala Arg Ala His Ser Ile
        115                 120                 125

Ala Leu Val Gln Gly Asn Ala Leu Gly Gly Gly Phe Glu Ala Ala Leu
    130                 135                 140

Ser Cys His Thr Ile Ile Ala Glu Glu Gly Val Met Met Gly Leu Pro
145                 150                 155                 160

Glu Val Leu Phe Asp Leu Phe Pro Gly Met Gly Ala Tyr Ser Phe Met
                165                 170                 175

Cys Gln Arg Ile Ser Ala His Leu Ala Gln Lys Ile Met Leu Glu Gly
            180                 185                 190

Asn Leu Tyr Ser Ala Glu Gln Leu Leu Gly Met Gly Leu Val Asp Arg
        195                 200                 205

Val Val Pro Arg Gly Gln Gly Val Ala Ala Val Glu Gln Val Ile Arg
```

-continued

```
    210                 215                 220

Glu Ser Lys Arg Thr Pro His Ala Trp Ala Ala Met Gln Gln Val Arg
225                 230                 235                 240

Glu Met Thr Thr Ala Val Pro Leu Glu Glu Met Met Arg Ile Thr Glu
                245                 250                 255

Ile Trp Val Asp Thr Ala Met Gln Leu Gly Glu Lys Ser Leu Arg Thr
            260                 265                 270

Met Asp Arg Leu Val Arg Ala Gln Ser Arg Arg Ser Gly Leu Asp Ala
        275                 280                 285

Gly


<210> SEQ ID NO 11
<211> LENGTH: 870
<212> TYPE: DNA
<213> ORGANISM: Stenotrophomonas maltophilia

<400> SEQUENCE: 11

atgtctgcag tacgccccat cattacccgt ccctcgcagc accctaccct gcgtatcacc      60

gaagaacccg agcgggatgt ttactggatc catatgcacg ccaacctggt caaccagcca     120

ggccggccgt gcttcgcctc acgcctggtc gatgacatcg tcgactacca gcgcgaactg     180

ggcgatcgcc tcagcgcctc gcacgctctg tcaccccatg tcgtacttgc ctctgacagc     240

gacgtgttca acctgggcgg cgatctcgaa ctgttctgcc gcctgatccg cgagggcgac     300

cgcgcccgcc tgctcgacta tgcccagcgc tgcgtgcgcg gcgtgcatgc cttccatgcc     360

ggcctgggca cccgtgccca cagcatcgcc ctggtccagg gcaatgcact gggggggcggc    420

ttcgaggccg cactgagctg ccacaccatc gtcgccgagg aaggcgtgtt gatgggcctg     480

ccggaggtgc tgttcgacct gttccccggc atgggcgcct actccttcct gtgccagcgg     540

atcagtccgc ggctggcgga gaagatcatg ctggaaggca acctctacac cgccagccag     600

ctgaaggaaa tgggcctggt cgacatcgtg gtgccggtgg gcgaaggtgt tgccgcagtc     660

gaacaggtga tcaaggaaag ccgacgcatc ccgcacgcct gggcggcgat gcgtgaggtc     720

aacgagatcg ccaccatggt gccgctgcat gaaatgatgc ggatcaccga gatctgggta     780

gacactgcga tgcagctcgg cgagaagtcc ctgcgcacca tggatcggct ggtacgggcg     840

caggcccggc gcaatggcga cccggcctga                                      870


<210> SEQ ID NO 12
<211> LENGTH: 870
<212> TYPE: DNA
<213> ORGANISM: Artificial Sequence
<220> FEATURE:
<223> OTHER INFORMATION: Oligonucleotide

<400> SEQUENCE: 12

atgtctgcgg ttcgtccgat catcacccgt ccgtctcagc acccgaccct gcgtatcacc      60

gaagaaccgg aacgtgacgt ttactggatc cacatgcacg cgaacctggt taaccagccg     120

ggtcgtccgt gcttcgcgtc tcgtctggtt gacgacatcg ttgactacca gcgtgaactg     180

ggtgaccgtc tgtctgcgtc tcacgcgctg tctccgcacg ttgttctggc gtctgactct     240

gacgttttca acctgggtgg tgacctggaa ctgttctgcc gtctgatccg tgaaggtgac     300

cgtgcgcgtc tgctggacta cgcgcagcgt tgcgttcgtg gtgttcacgc gttccacgcg     360

ggtctgggta cccgtgcgca ctctatcgcg ctggttcagg gtaacgcgct gggtggtggt     420

ttcgaagcgg cgctgtcttg ccacaccatc gttgcggaag aaggtgttct gatgggtctg     480
```

-continued

```
ccggaagttc tgttcgacct gttcccgggt atgggtgcgt actctttcct gtgccagcgt    540

atctctccgc gtctggcgga aaaaatcatg ctggaaggta acctgtacac cgcgtctcag    600

ctgaaagaaa tgggtctggt tgacatcgtt gttccggttg gtgaaggtgt tgcggcggtt    660

gaacaggtta tcaaagaatc tcgtcgtatc ccgcacgcgt gggcggcgat gcgtgaagtt    720

aacgaaatcg cgaccatggt tccgctgcac gaaatgatgc gtatcaccga aatctgggtt    780

gacaccgcga tgcagctggg tgaaaaatct ctgcgtacca tggaccgtct ggttcgtgcg    840

caggcgcgtc gtaacggtga cccggcgtga                                     870
```

```
<210> SEQ ID NO 13
<211> LENGTH: 289
<212> TYPE: PRT
<213> ORGANISM: Stenotrophomonas maltophilia

<400> SEQUENCE: 13

Met Ser Ala Val Arg Pro Ile Ile Thr Arg Pro Ser Gln His Pro Thr
1               5                   10                  15

Leu Arg Ile Thr Glu Glu Pro Glu Arg Asp Val Tyr Trp Ile His Met
            20                  25                  30

His Ala Asn Leu Val Asn Gln Pro Gly Arg Pro Cys Phe Ala Ser Arg
        35                  40                  45

Leu Val Asp Asp Ile Val Asp Tyr Gln Arg Glu Leu Gly Asp Arg Leu
    50                  55                  60

Ser Ala Ser His Ala Leu Ser Pro His Val Val Leu Ala Ser Asp Ser
65                  70                  75                  80

Asp Val Phe Asn Leu Gly Gly Asp Leu Glu Leu Phe Cys Arg Leu Ile
                85                  90                  95

Arg Glu Gly Asp Arg Ala Arg Leu Leu Asp Tyr Ala Gln Arg Cys Val
            100                 105                 110

Arg Gly Val His Ala Phe His Ala Gly Leu Gly Thr Arg Ala His Ser
        115                 120                 125

Ile Ala Leu Val Gln Gly Asn Ala Leu Gly Gly Gly Phe Glu Ala Ala
    130                 135                 140

Leu Ser Cys His Thr Ile Val Ala Glu Glu Gly Val Leu Met Gly Leu
145                 150                 155                 160

Pro Glu Val Leu Phe Asp Leu Phe Pro Gly Met Gly Ala Tyr Ser Phe
                165                 170                 175

Leu Cys Gln Arg Ile Ser Pro Arg Leu Ala Glu Lys Ile Met Leu Glu
            180                 185                 190

Gly Asn Leu Tyr Thr Ala Ser Gln Leu Lys Glu Met Gly Leu Val Asp
        195                 200                 205

Ile Val Val Pro Val Gly Glu Gly Val Ala Ala Val Glu Gln Val Ile
    210                 215                 220

Lys Glu Ser Arg Arg Ile Pro His Ala Trp Ala Ala Met Arg Glu Val
225                 230                 235                 240

Asn Glu Ile Ala Thr Met Val Pro Leu His Glu Met Met Arg Ile Thr
                245                 250                 255

Glu Ile Trp Val Asp Thr Ala Met Gln Leu Gly Glu Lys Ser Leu Arg
            260                 265                 270

Thr Met Asp Arg Leu Val Arg Ala Gln Ala Arg Arg Asn Gly Asp Pro
        275                 280                 285

Ala
```

-continued

<210> SEQ ID NO 14
<211> LENGTH: 819
<212> TYPE: DNA
<213> ORGANISM: Pseudomonas aeruginosa

<400> SEQUENCE: 14

```
atgaacactg ccgtcgaacc ctacaaggct tcctccttcg acctgaccca caagctcacc     60

gtggaaaagc acgggcacac cgcgctgatc accatcaacc acccgccggc caacacctgg    120

gaccgcgact cgctgatcgg cctgcgccaa ctgatcgagc acctcaaccg cgacgacgat    180

atctacgccc tggtagtgac cggccagggg ccgaagttct tctccgccgg cgccgacctg    240

aacatgttcg ccgacggcga caaggcccgc gctcgcgaga tggcccgccg cttcggcgaa    300

gccttcgagg cgctgcgcga tttccgcggg gtgtcgatcg cggcgatcaa cggctacgcc    360

atgggcggcg gcctggagtg cgccctcgcc tgcgacatcc gcatcgccga gcgccaggcg    420

cagatggccc tgccggaggc cgcggtgggc ctgctgccct gcgccggcgg gacccaggcg    480

ctgccctggc tggtgggcga aggctgggcc aagcggatga tcctctgcaa cgagcgggtg    540

gatgcggaaa ccgccctgcg catcggcctg gtcgaacagg tggtggacag cggcgaggcg    600

cgcggcgccg ccctgctgct ggcggccaag gtggcacgcc agagcccggt ggcgatccgc    660

accatcaagc cgctgatcca gggtgcccgc gaacgcgcgc cgaacacttg gctgccggag    720

gagcgcgagc gcttcgtcga tctgttcgac gcccaggaca cccgcgaagg ggtcaacgcc    780

ttcctcgaga agcgcgatcc caagtggcgc aactgctga                           819
```

<210> SEQ ID NO 15
<211> LENGTH: 820
<212> TYPE: DNA
<213> ORGANISM: Artificial Sequence
<220> FEATURE:
<223> OTHER INFORMATION: Oligonucleotide

<400> SEQUENCE: 15

```
atgaacaccg cggttgaacc gtacaaagcg tcttctttcg acctgaccca caaactgacc     60

gttgaaaaac acggtcacac cgcgctgatc accatcaacc acccgccggc gaacacctgg    120

gaccgtgact ctctgatcgg tctgcgtcag ctgatcgaac acctgaaccg tgacgacgac    180

atctacgcgc tggttgttac cggtcagggt ccgaaattct tctctgcggg tgcggacctg    240

aacatgttcg cggacggtga caaagcgcgt gcgcgtgaaa tggcgcgtcg tttcggtgaa    300

gcgttcgaag cgctgcgtga cttccgtggt gtttctatcg cggcgatcaa cggttacgcg    360

atgggtggtg gtctggaatg cgcgctggcg tgcgacatcc gtatcgcgga acgtcaggcg    420

cagatggcgc tgccggaagc ggcggttggt ctgctgccgt gcgcgggtgg tacccaggcg    480

ctgccgtggc tggttggtga aggttgggcg aaacgtatga tcctgtgcaa cgaacgtgtt    540

gacgcggaaa ccgcgctgcg tatcggtctg gttgaacagg ttgttgactc tggtgaagcg    600

cgtggtgcgg cgctgctgct ggcggcgaaa gttgcgcgtc agtctccggt tgcgatccgt    660

accatcaaac cgctgatcca gggtgcgcgt gaacgtgcgc cgaacacctg gctgccggaa    720

gaacgtgaac gtttcgttga cctgttcgac gcgcaggaca cccgtgaagg tgttaacgcg    780

ttcctggaaa aacgtgaccc gaaatggcgt aactgctgaa                          820
```

<210> SEQ ID NO 16
<211> LENGTH: 272
<212> TYPE: PRT
<213> ORGANISM: Pseudomonas aeruginosa

<400> SEQUENCE: 16

Met Asn Thr Ala Val Glu Pro Tyr Lys Ala Ser Ser Phe Asp Leu Thr
1               5                   10                  15

His Lys Leu Thr Val Glu Lys His Gly His Thr Ala Leu Ile Thr Ile
            20                  25                  30

Asn His Pro Pro Ala Asn Thr Trp Asp Arg Asp Ser Leu Ile Gly Leu
        35                  40                  45

Arg Gln Leu Ile Glu His Leu Asn Arg Asp Asp Asp Ile Tyr Ala Leu
    50                  55                  60

Val Val Thr Gly Gln Gly Pro Lys Phe Phe Ser Ala Gly Ala Asp Leu
65                  70                  75                  80

Asn Met Phe Ala Asp Gly Asp Lys Ala Arg Ala Arg Glu Met Ala Arg
                85                  90                  95

Arg Phe Gly Glu Ala Phe Glu Ala Leu Arg Asp Phe Arg Gly Val Ser
            100                 105                 110

Ile Ala Ala Ile Asn Gly Tyr Ala Met Gly Gly Gly Leu Glu Cys Ala
        115                 120                 125

Leu Ala Cys Asp Ile Arg Ile Ala Glu Arg Gln Ala Gln Met Ala Leu
    130                 135                 140

Pro Glu Ala Ala Val Gly Leu Leu Pro Cys Ala Gly Gly Thr Gln Ala
145                 150                 155                 160

Leu Pro Trp Leu Val Gly Glu Gly Trp Ala Lys Arg Met Ile Leu Cys
                165                 170                 175

Asn Glu Arg Val Asp Ala Glu Thr Ala Leu Arg Ile Gly Leu Val Glu
            180                 185                 190

Gln Val Val Asp Ser Gly Glu Ala Arg Gly Ala Ala Leu Leu Leu Ala
        195                 200                 205

Ala Lys Val Ala Arg Gln Ser Pro Val Ala Ile Arg Thr Ile Lys Pro
    210                 215                 220

Leu Ile Gln Gly Ala Arg Glu Arg Ala Pro Asn Thr Trp Leu Pro Glu
225                 230                 235                 240

Glu Arg Glu Arg Phe Val Asp Leu Phe Asp Ala Gln Asp Thr Arg Glu
                245                 250                 255

Gly Val Asn Ala Phe Leu Glu Lys Arg Asp Pro Lys Trp Arg Asn Cys
            260                 265                 270

<210> SEQ ID NO 17
<211> LENGTH: 870
<212> TYPE: DNA
<213> ORGANISM: Enterobacter cloacae subsp. cloacae

<400> SEQUENCE: 17
atgacagtta tcaatcaggc tacctgcaca ctgtttaccg atactgaacg tttcactcag 60
ttgtccgggt attatgagga ggagcgccgc acagtctgga tgatgttacg ggcgcagcca 120
cgaccttgct tcaaccatgc gttaatcgaa gagatcatga acctctcctg gctcgttcgc 180
cagtccgggt ttgcggtcga tttttgggtt accggttcgc tggtgcccga gatgtacaat 240
gcgggaggtg atttacagtt ctttgtcgaa tgtatccaaa acggacgccg cgaagcgtta 300
agagcctatg cccgtgcctg cgtggactgc gttcatgcgg cgtcacgggg gtttgatacg 360
ggggctatta ccctggcgat ggtcgaaggc agtgcgttag gggcggatt cgaagccgcg 420 ctggcgcacc actttgtgct gtcccagcgc gatgcccgct taggcttccc tgagatcgcc 480
ttcaaccttt tccccggcat gggggggtac tcgctggttg ctcgccgctc aggcatgaag 540

```
ctggcggagg agctcatcta caaaggggag tctcatacgg cagaatggta tgaacagcat    600

gggttagtgg atgtcctgtt cgaacccggg caaagttacg tctccgtcag aacgttcatt    660

gacacgctgc ggccgaagat gaacggcgta aaggcgatgt tacgcgcccg tacccgcgtg    720

ctgcagctgc ctcgcagcga gctgatggat atcacggaag attgggttga cgctgcgttc    780

tgccttgaac caaaagatat cgcctatatg gagcgtctgg tcatgctgca aaaccgccac    840

caggcggcgg gtttacgcaa agccagttag                                     870
```

```
<210> SEQ ID NO 18
<211> LENGTH: 287
<212> TYPE: PRT
<213> ORGANISM: Burkholderia cenocepacia

<400> SEQUENCE: 18

Met Gln Leu Gln Ser His Pro Ala Cys Arg Pro Phe Tyr Glu Ala Gly
1               5                   10                  15

Glu Leu Ser Gln Leu Thr Ala Phe Tyr Glu Glu Gly Arg Asn Val Met
            20                  25                  30

Trp Met Met Leu Arg Ser Glu Pro Arg Pro Cys Phe Asn Gln Gln Leu
        35                  40                  45

Val Thr Asp Ile Ile His Leu Ala Arg Val Ala Arg Asp Ser Gly Leu
    50                  55                  60

Thr Phe Asp Phe Trp Val Thr Gly Ser Leu Val Pro Glu Leu Phe Asn
65                  70                  75                  80

Val Gly Gly Asp Leu Ser Phe Phe Val Asp Ala Ile Arg Ser Gly Arg
                85                  90                  95

Arg Asp Gln Leu Met Ala Tyr Ala Arg Ser Cys Ile Asp Gly Val Tyr
            100                 105                 110

Glu Ile Tyr Thr Gly Phe Gly Thr Gly Ala Ile Ser Ile Ala Met Val
        115                 120                 125

Glu Gly Ser Ala Leu Gly Gly Gly Phe Glu Ala Ala Leu Ala His His
    130                 135                 140

Tyr Val Leu Ala Gln Lys Gly Val Lys Leu Gly Phe Pro Glu Ile Ala
145                 150                 155                 160

Phe Asn Leu Phe Pro Gly Met Gly Gly Tyr Ser Leu Val Ala Arg Lys
                165                 170                 175

Ala Asn Arg Gly Leu Ala Glu Ser Leu Ile Ala Thr Gly Glu Ala His
            180                 185                 190

Ala Ala Glu Trp Tyr Glu Asp Cys Gly Leu Ile Asp Glu Thr Phe Asp
        195                 200                 205

Ala Gly Asp Ala Tyr Leu Ala Thr Arg Thr Phe Ile Asp Val Thr Lys
    210                 215                 220

Pro Lys Leu Asn Gly Ile Arg Ala Met Leu Arg Ala Arg Glu Arg Val
225                 230                 235                 240

Phe Gln Leu Ser Arg Ser Glu Leu Met Asp Ile Thr Glu Ala Trp Val
                245                 250                 255

His Ala Ala Phe Thr Ile Glu Pro Lys Asp Leu Ala Tyr Met Glu Arg
            260                 265                 270

Leu Val Met Leu Gln Asn Arg Arg Val Ser Lys Leu Arg Thr Val
        275                 280                 285


<210> SEQ ID NO 19
<211> LENGTH: 288
<212> TYPE: PRT
```

```
<213> ORGANISM: Yersinia enterocolitica

<400> SEQUENCE: 19

Met Asn Met Ile Asn Leu Pro Ser Cys Arg Ser Phe Thr Glu Ala Gly
1               5                   10                  15

His Leu Ser Gln Ile Ser Ala Tyr Tyr Glu Glu Gly Arg Asn Thr Leu
            20                  25                  30

Trp Met Leu Leu Arg Ala His Pro Arg Pro Cys Phe Asn Leu Glu Leu
        35                  40                  45

Ile Glu Asn Ile Met Thr Leu Ala Gln Ala Ala Lys Glu Ser Lys Leu
    50                  55                  60

Pro Ile Asp Phe Trp Val Thr Gly Ser Val Val Pro Asn Met Phe Asn
65                  70                  75                  80

Val Gly Gly Asp Leu Asn Phe Phe Ala Gln Met Ile Lys Asn Arg Lys
                85                  90                  95

Arg Glu Ala Leu Met Ala Tyr Ala Arg Ala Cys Val Asp Cys Val His
            100                 105                 110

Ala Ala Ser Arg Gly Phe Asp Thr Gly Ala Ile Ser Ile Ala Met Ile
        115                 120                 125

Glu Gly Ser Ala Leu Gly Gly Gly Phe Glu Ala Ala Leu Ala His His
    130                 135                 140

Phe Val Leu Ala Gln Thr Thr Ala Arg Met Gly Phe Pro Glu Ile Ala
145                 150                 155                 160

Phe Asn Leu Phe Pro Gly Met Gly Gly Tyr Ser Leu Val Ala Arg Lys
                165                 170                 175

Ala Gly Met Arg Val Ala Glu Gln Leu Ile Trp Thr Gly Glu Ser His
            180                 185                 190

Ala Ala Glu Trp Tyr Glu Ser Arg Gly Leu Val Asp Lys Leu Phe Gln
        195                 200                 205

Pro Gly Asp Ala Tyr Ile Ala Thr Arg Thr Phe Ile Asp Thr Ile Arg
    210                 215                 220

Pro Lys Leu Asn Gly Met Arg Ala Met Val Arg Val Arg Gln Arg Val
225                 230                 235                 240

Leu Gln Leu Thr Arg Ser Glu Leu Met Asp Ile Thr Glu Asp Trp Val
                245                 250                 255

Asp Ser Ala Phe Ser Ile Glu Pro Lys Asp Ile Ala Tyr Ile Glu Arg
            260                 265                 270

Leu Val Thr Leu Gln Asp Arg His Thr Ser Gly Met Pro Lys Ala Ile
        275                 280                 285


<210> SEQ ID NO 20
<211> LENGTH: 288
<212> TYPE: PRT
<213> ORGANISM: Serratia marcescens

<400> SEQUENCE: 20

Met Lys Leu Phe Asn His Pro Thr Cys Arg Pro Phe Thr Glu Ala Gly
1               5                   10                  15

Asn Leu Ser Gln Leu Ser Ala Tyr Tyr Glu Glu Glu Arg His Ile Met
            20                  25                  30

Trp Met Leu Leu Arg Ala Ala Pro Arg Pro Cys Phe Asn Gln Ala Leu
        35                  40                  45

Ile Glu Asp Ile Met Thr Leu Ala Gln Ala Ala Lys Glu Ser Ser Leu
    50                  55                  60

Gln Phe Asp Phe Trp Val Thr Gly Ser Leu Val Pro Asn Met Phe Asn
```

-continued

```
65                  70                  75                  80

Val Gly Gly Asp Leu Gln Phe Phe Ala Glu Ala Ile Lys Asn Arg Lys
                85                  90                  95

Arg Glu Ala Met Met Ala Tyr Ala Arg Ala Cys Ile Asp Cys Val His
            100                 105                 110

Ala Ala Ala Arg Gly Phe Asp Thr Gly Ala Val Ser Ile Ala Met Val
        115                 120                 125

Glu Gly Ser Ala Leu Gly Gly Gly Phe Glu Ala Ala Leu Ala His His
    130                 135                 140

Phe Val Leu Ala Gln Asn Asn Ala Arg Met Gly Phe Pro Glu Ile Ala
145                 150                 155                 160

Phe Asn Leu Phe Pro Gly Met Gly Gly Tyr Ser Leu Val Ala Arg Lys
                165                 170                 175

Ala Gly Met Arg Leu Ala Glu Glu Leu Ile Trp Gly Gly Glu Ser His
            180                 185                 190

Thr Ala Glu Trp Phe Glu Ser Arg Gly Leu Val Asp Gln Leu Phe Gln
        195                 200                 205

Pro Gly Asp Ala Tyr Val Ala Thr Arg Thr Phe Ile Asp Thr Ile Arg
    210                 215                 220

Pro Lys Leu Asn Gly Met Arg Ala Met Leu Arg Ala Arg Gln Arg Val
225                 230                 235                 240

Leu Gln Leu Thr Arg Ser Glu Leu Met Asp Ile Thr Glu Asp Trp Val
                245                 250                 255

His Ala Ala Phe Thr Ile Glu Glu Lys Asp Arg Ala Tyr Ile Glu Arg
            260                 265                 270

Leu Val Met Leu Gln Asp Arg His Thr Leu Asn Leu Arg Arg Ala Gly
        275                 280                 285


<210> SEQ ID NO 21
<211> LENGTH: 288
<212> TYPE: PRT
<213> ORGANISM: Pantoea agglomerans

<400> SEQUENCE: 21

Met Thr Val Ile Asn Gln Ala Thr Cys Arg Leu Phe Thr Glu Val Gly
1               5                   10                  15

Asn Thr Thr Gln Leu Val Ala Tyr Tyr Glu Glu Gly Arg Arg Thr Met
            20                  25                  30

Trp Met Met Leu Arg Ala Gln Pro Arg Pro Ser Phe Asn His Glu Leu
        35                  40                  45

Ile Glu Glu Ile Met Asn Leu Ser Tyr Ala Ala Gln Arg Ser Gly Leu
    50                  55                  60

Pro Ile Asp Phe Trp Val Thr Gly Ser Leu Val Pro Gln Met Phe Asn
65                  70                  75                  80

Ala Gly Gly Asp Leu Arg Phe Phe Val Glu Cys Ile Arg Asn Asn Arg
                85                  90                  95

Arg Glu Ala Leu Arg Ala Tyr Ala Arg Ala Cys Val Asp Cys Ile His
            100                 105                 110

Ser Ala Ala Arg Gly Phe Asp Thr Gly Ala Val Thr Leu Ala Met Ile
        115                 120                 125

Glu Gly Ser Ala Leu Gly Gly Gly Phe Glu Ala Ala Leu Ala His His
    130                 135                 140

Phe Ile Leu Ala Gln Asn Asn Ala Arg Met Gly Phe Pro Glu Ile Ala
145                 150                 155                 160
```

-continued

```
Phe Asn Leu Phe Pro Gly Met Gly Gly Tyr Ser Leu Val Ala Arg Arg
                165                 170                 175

Ser Gly Met Lys Leu Ala Glu Glu Leu Ile Cys Glu Gly Glu Ser His
            180                 185                 190

Ser Ala Glu Trp Tyr Glu Thr Arg Gly Leu Val Asp Lys Val Phe Gln
        195                 200                 205

Pro Gly Asp Ser Tyr Arg Ala Thr Arg Thr Phe Ile Asp Thr Leu Arg
    210                 215                 220

Pro Lys Leu Asn Gly Val Arg Ala Met Leu Lys Ala Arg Gln Arg Val
225                 230                 235                 240

Leu Gln Leu Ser Arg Ala Glu Leu Met Asp Ile Thr Glu Asp Trp Val
                245                 250                 255

Asp Tyr Ala Phe Thr Ile Glu Ser Lys Asp Ile Ala Tyr Met Glu Arg
            260                 265                 270

Leu Val Gln Leu Gln Asn Arg His Ser Ala Ser Leu Arg Lys Ala Gly
        275                 280                 285


<210> SEQ ID NO 22
<211> LENGTH: 289
<212> TYPE: PRT
<213> ORGANISM: Cronobacter sakazakii

<400> SEQUENCE: 22

Met Ser Val Phe Asn Gln Ser Thr Cys Lys Leu Phe Thr Asp Thr Ala
1               5                   10                  15

Arg Phe Thr Gln Leu Ser Gly Phe Tyr Glu Glu Glu Arg Arg Ile Ile
            20                  25                  30

Trp Met Met Leu Arg Ala Gln Pro Arg Pro Cys Phe Asn His Ala Leu
        35                  40                  45

Ile Glu Asp Ile Met Asn Leu Ser Tyr Leu Val Gln Glu Ala Arg Leu
    50                  55                  60

Glu Val Asp Phe Trp Val Thr Gly Ser Leu Val Pro Gly Met Tyr Asn
65                  70                  75                  80

Thr Gly Gly Asp Leu Gln Phe Phe Val Asp Cys Ile Arg Asn Gly Arg
                85                  90                  95

Arg Glu Ala Leu Arg Ala Tyr Ala Arg Ala Cys Val Asp Cys Val His
            100                 105                 110

Ala Ala Ser Arg Gly Phe Asp Cys Gly Ala Ile Ser Leu Ala Met Val
        115                 120                 125

Glu Gly Ser Ala Leu Gly Gly Gly Phe Glu Ala Ala Leu Ala His His
    130                 135                 140

Phe Val Leu Ala Gln Arg Asp Val Arg Met Gly Phe Pro Glu Ile Ala
145                 150                 155                 160

Phe Asn Leu Phe Pro Gly Met Gly Gly Tyr Ser Leu Val Thr Arg Arg
                165                 170                 175

Ala Gly Met Arg Leu Ala Glu Glu Leu Ile Trp Gln Gly Glu Ser His
            180                 185                 190

Thr Ala Glu Trp Tyr Gln Pro Gln Gly Leu Val Asp Leu Leu Phe Glu
        195                 200                 205

Pro Gly Gln Gly Phe Val Ala Thr Arg Thr Phe Ile Asp Thr Leu Lys
    210                 215                 220

Pro Arg Leu Asn Gly Val Arg Ala Met Leu Arg Ala Arg Gln Arg Val
225                 230                 235                 240

Leu Arg Leu Ser Arg Asn Glu Leu Met Glu Ile Thr Glu Asp Trp Val
                245                 250                 255
```

```
Asp Ala Ala Phe Ser Leu Glu Pro Lys Asp Val Ser Tyr Met Glu Arg
            260                 265                 270

Leu Ile Gln Leu Gln Asn Arg His Thr Ala Ala Ala Leu Arg Lys Ala
        275                 280                 285

Gly
```

<210> SEQ ID NO 23
<211> LENGTH: 294
<212> TYPE: PRT
<213> ORGANISM: Achromobacter xylosoxidans

<400> SEQUENCE: 23

```
Met Asn Gln Leu Ile His Pro Asp Cys His Pro Phe Thr Ala Ala Gly
1               5                   10                  15

Asn Leu Lys Gln Val Ser Ala Phe Tyr Glu Glu Gly Arg Arg Val Met
            20                  25                  30

Trp Met Met Leu Arg Ala Gln Pro Arg Pro Cys Phe Asn His Glu Leu
        35                  40                  45

Ile Asp Glu Ile Met Thr Leu Ala Arg Ala Ala Lys Asp Ser Gly Leu
    50                  55                  60

Pro Ile Asp Phe Trp Val Thr Gly Ser Leu Val Pro Gln Ile Tyr Asn
65                  70                  75                  80

Val Gly Gly Asp Leu Asn Phe Phe Ala Glu Ala Ile Arg Thr Gly Arg
                85                  90                  95

Arg Glu Ala Leu Arg Ala Tyr Ala Arg Ala Cys Val Asp Cys Val His
            100                 105                 110

Ala Ala Thr Arg Gly Phe Asp Thr Gly Ala Val Ser Leu Ala Met Ile
        115                 120                 125

Glu Gly Thr Ala Leu Gly Gly Gly Phe Glu Ala Ala Leu Ala His His
    130                 135                 140

Phe Val Leu Ala Gln Asn Asn Ala Arg Met Gly Phe Pro Glu Met Ala
145                 150                 155                 160

Phe Asn Leu Phe Pro Gly Met Gly Gly Tyr Ser Leu Val Ala Arg Arg
                165                 170                 175

Ser Gly Met Lys Leu Ala Glu Glu Leu Ile Gly Ser Gly Glu Ser His
            180                 185                 190

Thr Ala Glu Trp Phe Gln Ala Arg Gly Leu Val Asp Val Leu Phe Glu
        195                 200                 205

Pro Gly Asp Ala Tyr Lys Ala Thr Arg Thr Phe Ile Asp Val Met Arg
    210                 215                 220

Pro Lys Leu Asn Gly Met Arg Ala Met Leu Arg Ala Arg Gln Arg Val
225                 230                 235                 240

Leu Gln Leu Thr Arg Ser Glu Leu Met Asp Ile Thr Glu Asp Trp Val
                245                 250                 255

Asp Ala Ala Phe Ser Ile Asp Pro Lys Asp Arg Ala Tyr Met Glu Arg
            260                 265                 270

Leu Val Met Ala Gln Asn Arg Arg Ser Pro Val Gly Pro Asp Gly Leu
        275                 280                 285

Ile Asp Ala Thr Met His
    290
```

<210> SEQ ID NO 24
<211> LENGTH: 289
<212> TYPE: PRT
<213> ORGANISM: Enterobacter cloacae subsp. cloacae -continued

<400> SEQUENCE: 24

```
Met Thr Val Ile Asn Gln Ala Thr Cys Thr Leu Phe Thr Asp Thr Glu
1               5                   10                  15

Arg Phe Thr Gln Leu Ser Gly Tyr Tyr Glu Glu Glu Arg Arg Thr Val
            20                  25                  30

Trp Met Met Leu Arg Ala Gln Pro Arg Pro Cys Phe Asn His Ala Leu
        35                  40                  45

Ile Glu Glu Ile Met Asn Leu Ser Trp Leu Val Arg Gln Ser Gly Phe
    50                  55                  60

Ala Val Asp Phe Trp Val Thr Gly Ser Leu Val Pro Glu Met Tyr Asn
65                  70                  75                  80

Ala Gly Gly Asp Leu Gln Phe Phe Val Glu Cys Ile Gln Asn Gly Arg
                85                  90                  95

Arg Glu Ala Leu Arg Ala Tyr Ala Arg Ala Cys Val Asp Cys Val His
            100                 105                 110

Ala Ala Ser Arg Gly Phe Asp Thr Gly Ala Ile Thr Leu Ala Met Val
        115                 120                 125

Glu Gly Ser Ala Leu Gly Gly Gly Phe Glu Ala Ala Leu Ala His His
    130                 135                 140

Phe Val Leu Ser Gln Arg Asp Ala Arg Leu Gly Phe Pro Glu Ile Ala
145                 150                 155                 160

Phe Asn Leu Phe Pro Gly Met Gly Gly Tyr Ser Leu Val Ala Arg Arg
                165                 170                 175

Ser Gly Met Lys Leu Ala Glu Glu Leu Ile Tyr Lys Gly Glu Ser His
            180                 185                 190

Thr Ala Glu Trp Tyr Glu Gln His Gly Leu Val Asp Val Leu Phe Glu
        195                 200                 205

Pro Gly Gln Ser Tyr Val Ser Val Arg Thr Phe Ile Asp Thr Leu Arg
    210                 215                 220

Pro Lys Met Asn Gly Val Lys Ala Met Leu Arg Ala Arg Thr Arg Val
225                 230                 235                 240

Leu Gln Leu Pro Arg Ser Glu Leu Met Asp Ile Thr Glu Asp Trp Val
                245                 250                 255

Asp Ala Ala Phe Cys Leu Glu Pro Lys Asp Ile Ala Tyr Met Glu Arg
            260                 265                 270

Leu Val Met Leu Gln Asn Arg His Gln Ala Ala Gly Leu Arg Lys Ala
        275                 280                 285

Ser
```

RECOMBINANT BACTERIA PRODUCING CHEMICALS INHIBITORY TO *Salmonella* INVASION

CROSS REFERENCE TO RELATED APPLICATION

This application is the National Phase of PCT/US2021/025037, filed Mar. 31, 2021, which claims the benefit of priority from U.S. Provisional Application No. 63/003,525, filed Apr. 1, 2020, the entire contents of which are incorporated herein by reference.

STATEMENT REGARDING FEDERALLY SPONSORED RESEARCH OR DEVELOPMENT

This invention was made with government support under 2017-67017-26571 awarded by the National Institute of Food and Agriculture. The government has certain rights in the invention.

INCORPORATION BY REFERENCE OF SEQUENCE LISTING

The Sequence Listing in an ASCII text file, named as 38154_9333_03US_SequenceListing.txt of 45 KB, created on Sep. 28, 2022, and submitted to the United States Patent and Trademark Office via EFS-Web, is incorporated herein by reference.

BACKGROUND

Non-typhoidal salmonellosis, caused by serovars of *Salmonella enterica* subspecies *enterica*, remains a leading cause of death among foodborne bacterial diseases both domestically and globally. Antibiotics, the typical response to bacterial infections, are seldom useful and risk the spread of resistance.

Fatty acids with a cis-2 double bond are produced in a number of bacterial species. These are used for quorum sensing and are termed diffusible signal factors (DSFs).

DSFs are produced in nature by a number of gram-negative bacteria, including species of the genera *Xanthomonas, Burkholderia, Stenotrophomonas* and *Xylella*, in which they are used as quorum-sensing signals. The production of these chemicals is encoded by an enoyl-CoA hydratase that introduces a cis-2 double bond during the synthesis of long-chain fatty acids.

SUMMARY OF THE DISCLOSURE

An aspect of the disclosure is directed to a genetically engineered bacterium, wherein the genetically engineered bacterium comprises an exogenous nucleic acid encoding an enzyme that produces a diffusible signal factor (DSF) by introducing a cis-2 double bond to a fatty acid.

In some embodiments, the enzyme is selected from the group consisting of an enzyme encoded by the AAO28287 (rpfF) locus of *Xylella fastidiosa*, and an enzyme encoded by the CAR54439 locus from *Burkholderia cenocepacia*, an enzyme encoded by the TWR33075 locus of *Cronobacter turicensis*, an enzyme encoded by the WP_129362672 locus of *Enterobacter cloacae*, an enzyme encoded by the NP_249436 locus of *Pseudomonas aeruginosa*, an enzyme encoded by the WP_005416390 locus of *Stenotrophomonas maltophilia*, an enzyme encoded by the AAM41146 locus of *Xanthomonas campestris* pathovar *campestris*, an enzyme encoded by the WP_054444565 locus of *Achromobacter xylosoxidans*, an enzyme encoded by the WP_085344885 locus of *Cronobacter sakazakii*, an enzyme encoded by the WP_124890011 locus of *Pantoea agglomerans*, an enzyme encoded by the WP_148874552 locus of *Serratia marcescens*, and an enzyme encoded by the AKF40192 locus of *Yersinia enterocolitica.*

In some embodiments, the enzyme is an enzyme encoded by the AAO28287 (rpfF) locus of *Xylella fastidiosa.*

In some embodiments, the exogenous nucleic acid comprises a sequence that is at least 80% identical to a sequence selected from the group consisting of SEQ ID NOs: 2, 3, 4, 5, 6, 8, 9, 11, 12, 14, 15, and 17.

In some embodiments, the exogenous nucleic acid encodes an amino acid sequence that is at least 80% identical to a sequence selected from the group consisting of SEQ ID NOs: 1, 7, 10, 13, 16, and 18-24.

In some embodiments, the genetically engineered bacterium is a probiotic bacterium.

In some embodiments, the probiotic bacterium is selected from the group consisting of genera *Escherichia, Propionibacterium, Lactobacillus, Bifidobacterium* and *Streptococcus*. In some embodiments, the probiotic bacterium is selected from the group consisting of *Escherichia coli* strain Nissle 1917, *Escherichia coli* strain MG1655, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*; and *Propionibacterium freudenreichii.*

In some embodiments, the genetically engineered bacterium is from the genus *Salmonella*. In some embodiments, the nucleic acid encoding the selected enzyme is codon-optimized for expression in the genetically engineered bacterium.

In some embodiments, the enzyme is expressed in the bacteria.

In some embodiments, the exogenous nucleic acid comprises a promoter selected from an endogenous promoter, a constitutive promoter and an inducible promoter.

In some embodiments, the exogenous nucleic acid is stably integrated in the bacterial genome. In some embodiments, a single copy of the exogenous nucleic acid is integrated in the bacterial genome.

In some embodiments, the present disclosure is directed to a composition, comprising the genetically engineered bacterium described herein, and a pharmaceutically or veterinarily acceptable carrier. In some embodiments, the composition is an animal feed composition.

Another aspect of the disclosure is directed to a method for treating or preventing a *Salmonella* infection comprising administering to a subject in need of treatment an effective amount of a genetically engineered bacterium, wherein the genetically engineered bacterium comprises an exogenous nucleic acid encoding an enzyme that produces a diffusible signal factor (DSF) by introducing a cis-2 double bond to a fatty acid.

In some embodiments, the enzyme is selected from the group consisting of an enzyme encoded by the AAO28287 (rpfF) locus of *Xylella fastidiosa*, and an enzyme encoded by the CAR54439 locus from *Burkholderia cenocepacia*, an enzyme encoded by the TWR33075 locus of *Cronobacter turicensis*, an enzyme encoded by the WP_129362672 locus of *Enterobacter cloacae*, an enzyme encoded by the NP_249436 locus of *Pseudomonas aeruginosa*, an enzyme encoded by the WP_005416390 locus of *Stenotrophomonas*

*maltophilia*, an enzyme encoded by the AAM41146 locus of *Xanthomonas campestris* pathovar *campestris*, an enzyme encoded by the WP_054444565 locus of *Achromobacter xylosoxidans*, an enzyme encoded by the WP_085344885 locus of *Cronobacter sakazakii*, an enzyme encoded by the WP_124890011 locus of *Pantoea agglomerans*, an enzyme encoded by the WP_148874552 locus of *Serratia marcescens*, and an enzyme encoded by the AKF40192 locus of *Yersinia enterocolitica.*

In some embodiments, the enzyme is an enzyme encoded by the AAO28287 (rpfF) locus of *Xylella fastidiosa.*

In some embodiments, the exogenous nucleic acid comprises a sequence that is at least 80% identical to a sequence selected from the group consisting of SEQ ID NOs: 2, 3, 4, 5, 6, 8, 9, 11, 12, 14, 15, and 17.

In some embodiments, the exogenous nucleic acid encodes an amino acid sequence that is at least 80% identical to a sequence selected from the group consisting of SEQ ID NOs: 1, 7, 10, 13, 16, and 18-24.

In some embodiments, the genetically engineered bacterium is a probiotic bacterium.

In some embodiments, the probiotic bacterium is selected from the group consisting of genera *Escherichia, Propionibacterium, Lactobacillus, Bifidobacterium* and *Streptococcus*. In some embodiments, the probiotic bacterium is selected from the group consisting of *Escherichia coli* strain Nissle 1917, *Escherichia coli* strain MG1655, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*; and *Propionibacterium freudenreichii.*

In some embodiments, the genetically engineered bacterium is from the genus *Salmonella*. In some embodiments, the nucleic acid encoding the selected enzyme is codon-optimized for expression in the genetically engineered bacterium.

In some embodiments, the enzyme is expressed in the bacteria.

In some embodiments, the exogenous nucleic acid comprises a promoter selected from an endogenous promoter, a constitutive promoter and an inducible promoter.

In some embodiments, the exogenous nucleic acid is stably integrated in the bacterial genome. In some embodiments, a single copy of the exogenous nucleic acid is integrated in the bacterial genome.

In some embodiments, the genetically engineered bacterium or a spore of the genetically engineered bacterium is within a capsule when administered.

In some embodiments, the subject is a human. In some embodiments, the subject is a non-human animal. In some embodiments, the non-human animal is a domesticated animal.

Another aspect of the disclosure is directed to a vector comprising a nucleic acid encoding an enzyme selected from the group consisting of an enzyme encoded by the AAO28287 (rpfF) locus of *Xylella fastidiosa*, and an enzyme encoded by the CAR54439 locus from *Burkholderia cenocepacia*, an enzyme encoded by the TWR33075 locus of *Cronobacter turicensis*, an enzyme encoded by the WP_129362672 locus of *Enterobacter cloacae*, an enzyme encoded by the NP_249436 locus of *Pseudomonas aeruginosa*, an enzyme encoded by the WP_005416390 locus of *Stenotrophomonas maltophilia*, an enzyme encoded by the AAM41146 locus of *Xanthomonas campestrispathovar campestris*, an enzyme encoded by the WP_054444565 locus of *Achromobacter xylosoxidans*, an enzyme encoded by the WP_085344885 locus of *Cronobacter sakazakii*, an enzyme encoded by the WP_124890011 locus of *Pantoea agglomerans*, an enzyme encoded by the WP_148874552 locus of *Serratia marcescens*, and an enzyme encoded by the AKF40192 locus of *Yersinia enterocolitica.*

In some embodiments, the enzyme is an enzyme encoded by the AAO28287 (rpfF) locus of *Xylella fastidiosa.*

In some embodiments, the nucleic acid encoding the selected enzyme is codon-optimized for expression in a bacterium.

In some embodiments, the nucleic acid comprises a sequence that is at least 80% identical to a sequence selected from the group consisting of SEQ ID NOs: 2, 3, 4, 5, 6, 8, 9, 11, 12, 14, 15, and 17.

In some embodiments, the nucleic acid encodes an amino acid sequence that is at least 80% identical to a sequence selected from the group consisting of SEQ ID NOs: 1, 7, 10, 13, 16, and 18-24.

In some embodiments, the vector further comprises a promoter selected from a native promoter, a heterologous promoter, a constitutive promoter or an inducible promoter.

Another aspect of the disclosure is directed to a method of producing a diffusible signal factor (DSF), comprising culturing the genetically engineered bacterium of any one of claims 1-14 under conditions that allow the genetically engineered bacterium to express the enzyme that produces a DSF, thereby producing the DSF. In some embodiments, the method of producing a diffusible signal factor (DSF) further comprises purifying the produced DSF from the cell culture.

DETAILED DESCRIPTION

Figure 1:
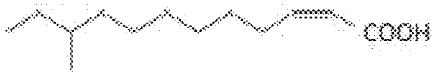
FIG. 1. Exemplary DSF molecules (adapted from: Zhou, L. et al., (2017). Trends in Microbiology, 25(4), 293-303.).
Figure 1:
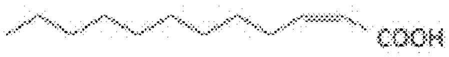
Figure 1:
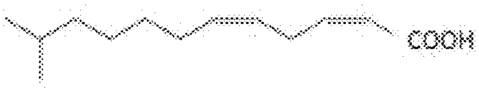
Figure 1:
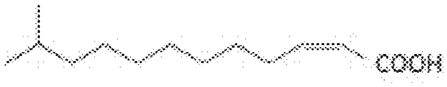
Figure 1:
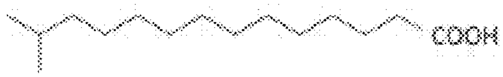
Figure 1:
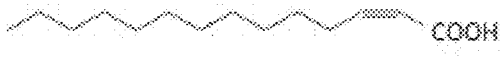
Figure 1:
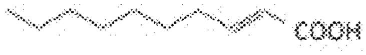
Figure 1:
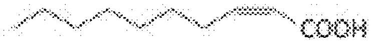
Figure 1:
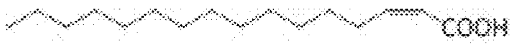
Figure 1:
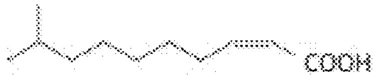
Figure 1:
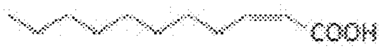
Figure 2:
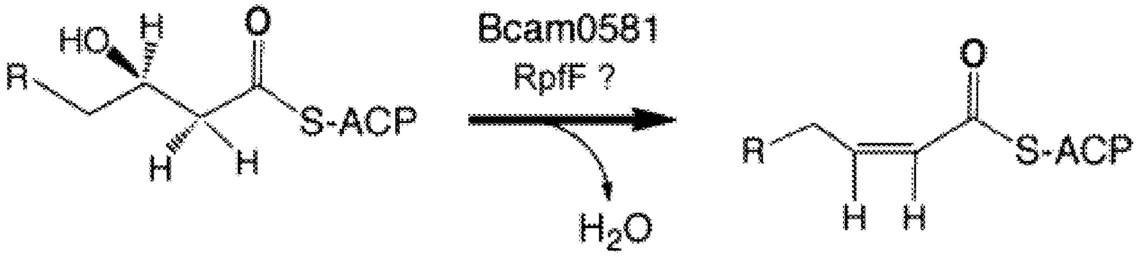
FIG. 2. A single enzyme is required to derive diffusible signal factors (DSFs) from the fatty-acid synthesis pathway (adapted from: Bi, Hongkai, et al Molecular Microbiology 83.4 (2012): 840-855).
Figures 3A, 3B, 3C:
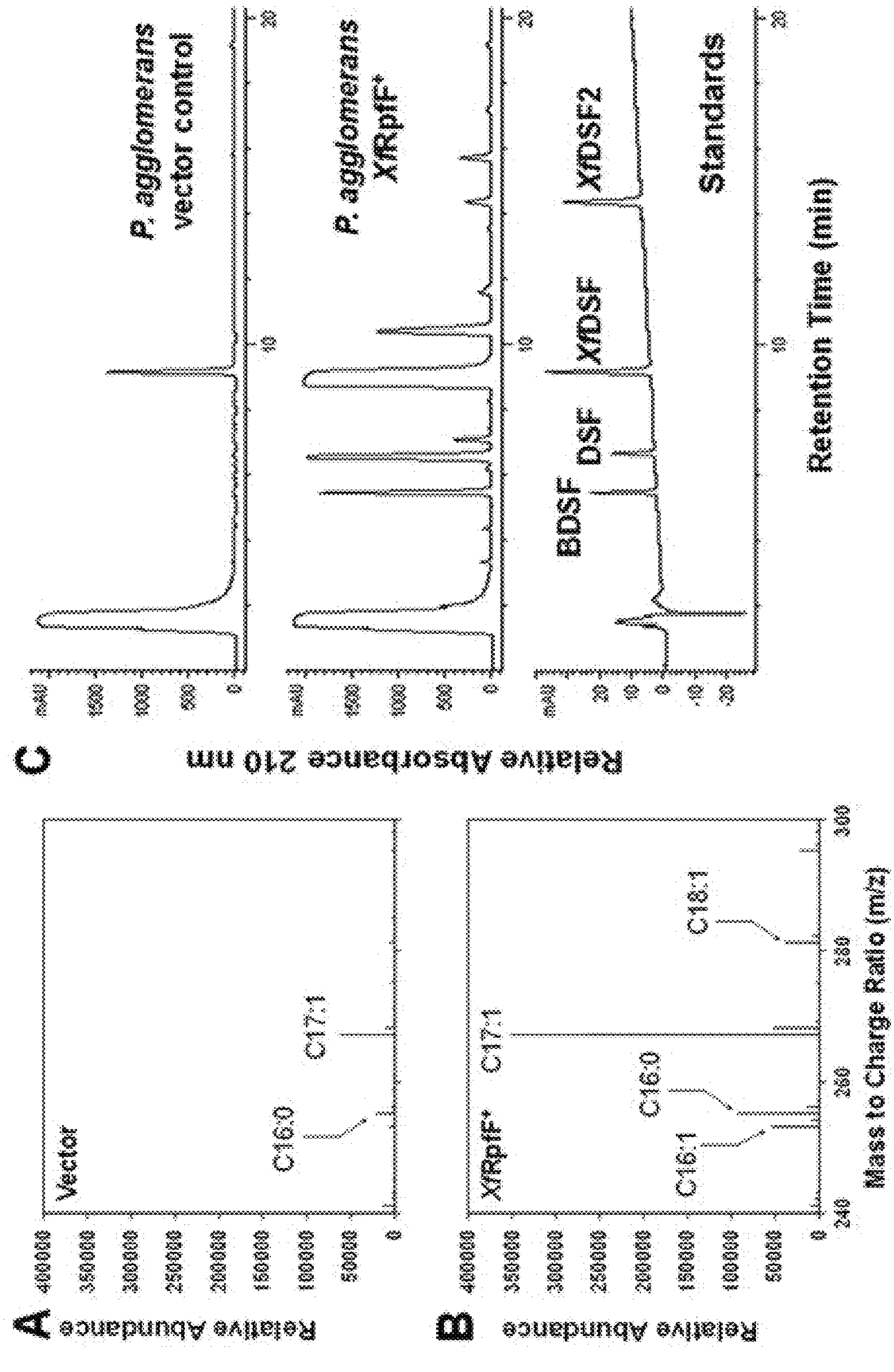
FIGS. 3A-3C. DSFs can be produced recombinantly. Here, rpfF of *Xylella fastidiosa* was cloned into *Pantoea agglomerans*. Electrospray ionization mass spectra (ESI-MS) of DSF-containing culture extracts of *Pantoea agglomerans* 299R harboring a vector only (A) or expressing XfRpfF (B). (C) High-performance liquid chromatographs (HPLC) analysis of *Pantoea agglomerans* 299R harboring a vector only (top panel) or expressing XfRpfF (middle panel) or solutions (250 μM) of synthetic standards (adapted from: Ionescu, Michael, et al., *M. Bio,* 7.4 (2016): e01054-16.).
Figure 4:
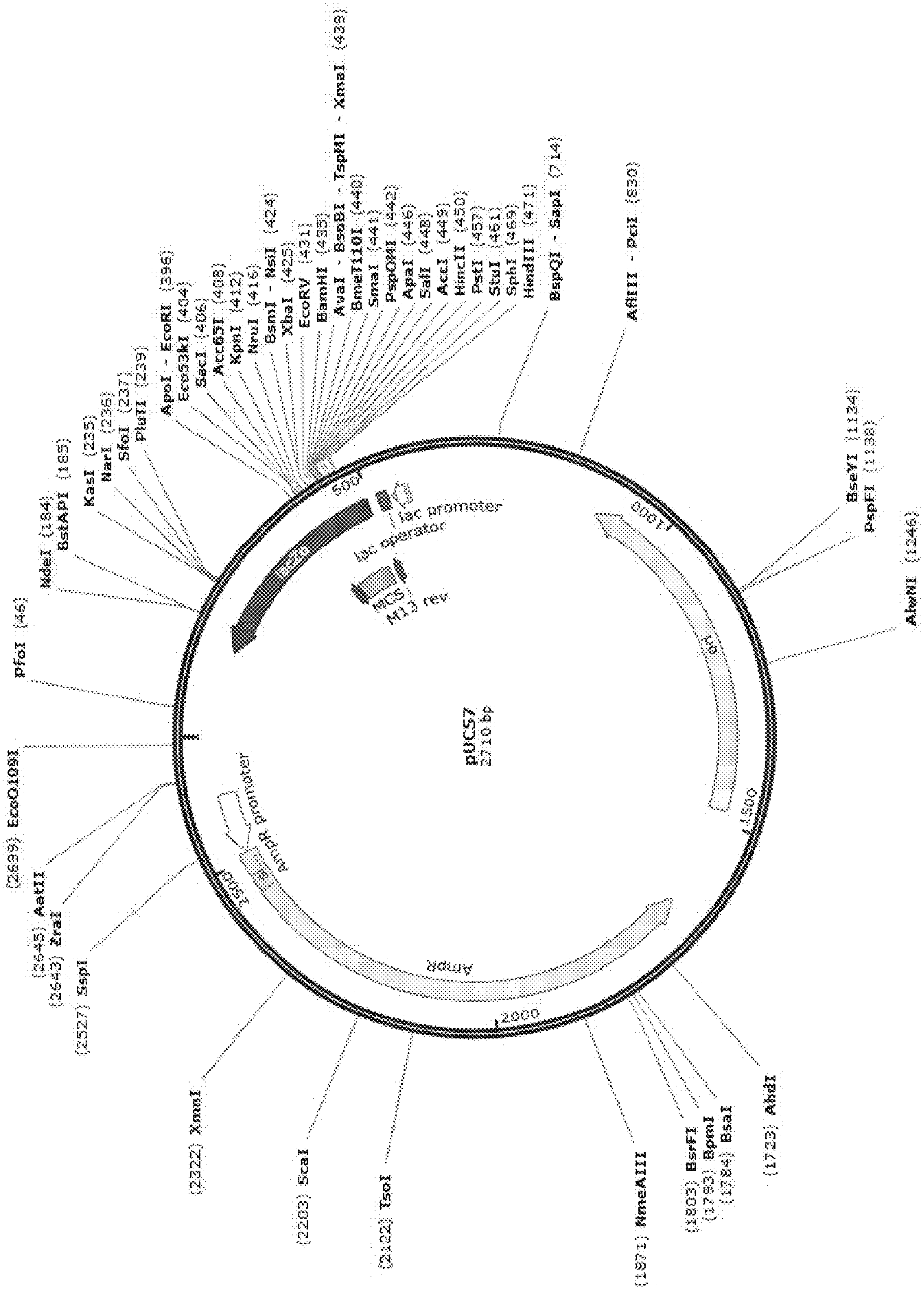
FIG. 4. pUC57 plasmid schematic used in the experiments. rpfF from *Xylella* or BCAM0581 from *Burkholderia*. Codon optimized for expression in *E. coli* and under the control of a constitutive promoter. Cloned into the EcoRV site of the pUC57 plasmid.

It has been found in this disclosure that *Salmonella* can be controlled not by trying to kill it, but instead by reducing its virulence through inhibition of the invasion of the intestinal epithelium, a necessary virulence function of this pathogen. It has been found in this disclosure that expression of a single gene in a bacterium (e.g., rpfF in *Xylella fastidiosa*, BCAM0581 in *Burkholderia cenocepacia* or their homologs described herein) produces a diffusible signal factor (a cis-2 unsaturated fatty acid) that inhibits the expression of *Salmonella* genes essential for invasion. The term "expression" refers to the process of converting genetic information of a polynucleotide into RNA through transcription, which is catalyzed by an enzyme, RNA polymerase and into protein, through translation of mRNA on ribosomes.

It has been found herein that a single enzyme is required to derive diffusible signal factors from the fatty-acid synthesis pathway. Long-chain fatty acids are produced through the sequential addition of carbons to create cell membrane components. A crotonase homolog, termed and rpfF in *Xylella fastidiosa*, introduces the cis-2 double bond into a fatty acid, producing a DSF. In *Burkholderia cenocepacia* the primary product is 2-cis-dodecenoic acid, while in *Xylella fastidiosa* they are 2-cis-hexadecenoic and 2-cis-tetradecenoic acid.

In some embodiments, the resulting recombinant bacteria are used to produce DSF compounds to be administered orally to humans, livestock animals and poultry. In some embodiments, the resulting recombinant bacteria are directly administered to a subject, to reduce infection and colonization by non-typhoidal *Salmonella* serovars through inhibiting the ability of *Salmonella* to penetrate the intestinal epithelial layer.

The specific virulence trait to be targeted is essential to the success of this approach: Invasion of the intestinal epithelium by *Salmonella* inflames the intestinal lumen, creating an environment that promotes the growth of *Salmonella* within the gut, while the invading bacteria themselves die. The implications of this lifecycle are paramount to the development of this novel means to prevent *Salmonella* infections. Resistance to any anti-*Salmonella* drug may occur, as it has for antimicrobials, through bacterial mutations. Targeting invasion as a means to control salmonellosis, however, prevents the propagation of this resistance. Because invading bacteria are killed in the process, the small number of resistant mutants that arise may provide some brief, temporary advantage in infection, but will not proliferate to pass on their resistance trait. Thus, *Salmonella* is very unlikely to gain resistance to drugs that inhibit invasion because resistant mutants are destined to die during the invasion process and so will not become fixed in the population. The disclosure therefore exploits this step in *Salmonella* pathogenesis by using diffusible signal factors (e.g., cis-2 unsaturated fatty acids) that specifically inhibit invasion, thereby producing a durable class of preventatives and therapeutics.

Diffusible Signal Factors (DSFs)

Specific compounds of "Diffusible Signal Factors" ("DSFs") have been identified herein that inhibit *Salmonella* invasion. DFSs affect quorum sensing systems in pathogenic bacteria including *Salmonella* that coordinate expression of virulence factors.

In some embodiments, a DSF is an unsaturated fatty acid with a cis-oriented double bond at position 2 relative to the carboxyl group, also referred to as "cis-2 unsaturated fatty acids". In some embodiments, a DSF is a cis-2 unsaturated fatty acid having a total number of carbon atoms of 10 to 30, i.e., any number between 10 and 30. A specific inhibitory fatty acid is (Z)-hexadec-2-enoic acid (common name 2-cis-hexadecenoic acid).

In some embodiments, a DSF comprises a cis-unsaturated fatty acid of the formula:

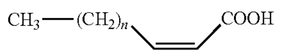
(1)

wherein n is an integer between 6 and 26. In some embodiments, n is 6, 7, 8, 9, 10, 11, 12, 13, 14, 15, or 16.

In some embodiments, n is an integer of 6-26, which corresponds to a number of carbon atoms of 10-30. In different embodiments, n may be, for example, 10, 12, 14, 16, 18, 20, 22, 24, or 26, or a value within a range bounded by any two of the foregoing values (e.g., 8-26, 8-24, 8-22, 8-20, 10-26, 10-24, 10-22, 10-20, 12-26, 12-24, 12-22, 12-20, 12-18, 14-20, or 14-18). Notably, the cis-2-unsaturated fatty acid shown in Formula (1) optionally includes a second carbon-carbon double bond resulting from removal of two hydrogen atoms on adjacent carbon atoms. In some embodiments, the cis-2-unsaturated fatty acid shown in Formula (1) optionally includes a third or fourth carbon-carbon double bond (resulting from removal of two pairs or three pairs, respectively, of hydrogen atoms on equivalent pairs of adjacent carbon atoms). Branched unsaturated fatty acids according to Formula (1) contain precisely or at least one, two, or three of the hydrogen atoms in methylene groups in Formula (1) substituted by an equivalent number of methyl groups, provided that the total number of carbon atoms within the branched fatty acid remains within the range of 10-30.

Some examples of these types of fatty acids include cis-2-decenoic acid (i.e., (Z)-dec-2-enoic acid), trans-2-decenoic acid, cis-9-methyl-2-decenoic acid, trans-9-methyl-2-decenoic acid, cis-2-undecenoic acid, trans-2-undecenoic acid, cis-5-methyl-2-undecenoic acid, trans-5-methyl-2-undecenoic acid, cis-2-dodecenoic acid (i.e., (Z)-dodec-2-enoic acid), trans-2-dodecenoic acid, cis-11-methyl-2-dodecenoic acid, trans-11-methyl-2-dodecenoic acid, cis-10-methyl-2-dodecenoic acid, trans-10-methyl-2-dodecenoic acid, cis-5-methyl-2-tridecenoic acid, trans-5-methyl-2-tridecenoic acid, trans-2,5-dimethyl-2-tridecenoic acid, cis-2-tetradecenoic acid, trans-2-tetradecenoic acid, cis-2-hexadecenoic acid (i.e., (Z)-hexadec-2-enoic acid), cis-2-icosenoic acid (i.e., (Z)-icos-2-enoic acid), cis-2,4,6-trimethyl-2-tetracosenoic acid, cis,cis-2,5-dodecadienoic acid, trans,trans-2,5-dodecadienoic acid, and cis,cis-11-methyl-2,5-dodecadienoic acid.

In some embodiments, any of the types of fatty acids described above may or may not be substituted with an additional carboxylic acid (or carboxylate) group, or with a hydroxy group, by replacing one of the shown hydrogen atoms in the above formula with a carboxylic acid or hydroxy group. In the case of an additional carboxylic acid group, the fatty acid is a di-acid, e.g., sebacic acid, undecanedioic acid, dodecanedioic acid, tridecanedioic acid, 2-decenedioic acid, and dodec-2-enedioic acid (traumatic acid). Some examples of fatty acids containing a hydroxy group include 2-hydroxydecanoic acid, 3-hydroxydecanoic acid, 2-hydroxydodecanoic acid, 12-hydroxydodecanoic acid, 2-hydroxytetradecanoic acid, 2-hydroxyhexadecanoic acid, 10-hydroxy-2-decenoic acid (also known as queen bee acid), and 10-hydroxy-8-decynoic acid. The fatty acid may also include one or two oxo (keto) groups, as in 3-oxodecanoic acid or trans-9-oxo-2-decenoic acid. In some embodiments, an additional carboxylic acid group and/or hydroxy group, and/or any other additional substituent (e.g., oxo), is not present in the fatty acid. In some embodiments, the fatty acid contains solely a linear or branched saturated or unsaturated hydrocarbon portion and a single carboxylic acid group.

In some embodiments, the DSF is selected from the group consisting of (Z)-hexadec-2-enoic acid, (Z)-dec-2-enoic acid, (Z)-dodec-2-enoic acid, and (Z)-icos-2-enoic acid (common names 2-cis-decenoic, 2-cis-dodecenoic and 2-cis-eicosenoic acids, respectively).

Enzymes Capable of Producing DSFs

In one aspect, the disclosure is directed to an enzyme capable of producing DSFs. In some embodiments, an enzyme capable of producing DSFs introduces a cis-2 double bond to a fatty acid. In some embodiments, the enzyme introduces a cis-2 double bond to a fatty acid of between 10-30 carbon atoms.

In some embodiments, the enzyme is selected from the group consisting of an enzyme encoded by the AAO28287 (rpfF) locus of *Xylella fastidiosa*, and an enzyme encoded by the CAR54439 locus from *Burkholderia cenocepacia*, an enzyme encoded by the TWR33075 locus of *Cronobacter turicensis*, an enzyme encoded by the WP_129362672 locus of *Enterobacter cloacae*, an enzyme encoded by the NP_249436 locus of *Pseudomonas aeruginosa*, an enzyme encoded by the WP_005416390 locus of *Stenotrophomonas maltophilia*, an enzyme encoded by the AAM41146 locus of *Xanthomonas campestris* pathovar *campestris*, an enzyme encoded by the WP_054444565 locus of *Achromobacter xylosoxidans*, an enzyme encoded by the WP_085344885 locus of *Cronobacter sakazakii*, an enzyme encoded by the WP_124890011 locus of *Pantoea agglomerans*, an enzyme encoded by the WP_148874552 locus of *Serratia marcescens*, and an enzyme encoded by the AKF40192 locus of *Yersinia enterocolitica*. In a specific embodiment, the enzyme is an enzyme encoded by the AAO28287 (rpfF) locus of *Xylella fastidiosa*.

In some embodiments, the enzyme is encoded by a homolog of the AAO28287 (rpfF) locus of *Xylella fastidiosa*. The term "homolog" refers to genes or their encoded polypeptides as related to each other in that the genes are related to each other by descent from a common ancestral DNA sequence, and therefore, the corresponding polynucleotide sequences of the genes have substantial sequence identity, and the encoded polypeptides have substantial sequence identity (identical residues) or similarity (residues with similar physicochemical properties, e.g., see Table 1).

TABLE 1

| Groups of amino acids with similar physicochemical properties | | |
|---|---|---|
| Group | Amino acids | 1-letter code |
| Aliphatic | Glycine, Alanine, Valine, Leucine, Isoleucine | G, A, V, L, I |
| Hydroxyl or sulfur/selenium-containing | Serine, Cysteine, Selenocysteine, Threonine, Methionine | S, C, U, T, M |
| Cyclic | Proline | P |
| Aromatic | Phenylalanine, Tyrosine, Tryptophan | F, Y, W |
| Basic | Histidine, Lysine, Arginine | H, K, R |
| Acidic and their amides | Aspartate, Glutamate, Asparagine, Glutamine | D, E, N, Q |

By "substantial" in referring to sequence identity or similarity it means at least 35%, at least 40%, at least 50%, at least 55%, at least 60%, at least 65%, at least 66%, at least 68%, at least 70%, at least 75%, at least 80%, at least 86%, at least 88%, at least 90%, at least 92%, at least 95%, at least 97%, or at least 99% sequence identity or similarity. Homolog genes generally encode polypeptides having the same or similar functions.

In some embodiments, an "rpfF gene homolog" encodes an enzyme that has substantial sequence identity (i.e., at least 40%, at least 60%, at least 65%, at least 66%, at least 68%, at least 70%, at least 75%, at least 80%, at least 86%, at least 88%, at least 90%, at least 92%, at least 95%, at least 97%, or at least 99% sequence identity) to the rpfF protein of *Xylella fastidiosa* Temecula1 shown by SEQ ID NO: 1. In some embodiments, an "rpfF gene homolog" encodes an enzyme that has a function that is equivalent to the function of the rpfF protein of *Xylella fastidiosa* Temecula1 shown by SEQ ID NO: 1 (e.g., the function of introducing a cis-2 double bond).

Several genera encode enoyl-CoA hydratase genes encoding enzymes with homology to *Xylella fastidiosa* RpfF. Representative species that have rpfF gene homologs are shown in Table 2. The degree of homology between different RpfF homolog proteins is shown in Table 3.

In some embodiments, the enzyme comprises an amino acid sequence that is at least 80%, at least 85%, at least 90%, at least 95%, at least 99% or more identical to a sequence selected from the group consisting of SEQ ID NOs: 1, 7, 10, 13, 16, and 18-24.

In some embodiment, the enzyme comprises an amino acid sequence that is at least 80%, at least 85%, at least 90%, at least 95%, at least 99% or more identical to SEQ ID NO: 1.

In some embodiment, the enzyme comprises an amino acid sequence that is at least 80%, at least 85%, at least 90%, at least 95%, at least 99% or more identical to SEQ ID NO: 7.

In some embodiment, the enzyme comprises an amino acid sequence that is at least 80%, at least 85%, at least 90%, at least 95%, at least 99% or more identical to SEQ ID NO: 10.

In some embodiment, the enzyme comprises an amino acid sequence that is at least 80%, at least 85%, at least 90%, at least 95%, at least 99% or more identical to SEQ ID NO: 13.

In some embodiment, the enzyme comprises an amino acid sequence that is at least 80%, at least 85%, at least 90%, at least 95%, at least 99% or more identical to SEQ ID NO: 16.

In some embodiment, the enzyme comprises an amino acid sequence that is at least 80%, at least 85%, at least 90%, at least 95%, at least 99% or more identical to SEQ ID NO: 18.

In some embodiment, the enzyme comprises an amino acid sequence that is at least 80%, at least 85%, at least 90%, at least 95%, at least 99% or more identical to SEQ ID NO: 19.

TABLE 2

| RpfF homologs in bacterial species | | | |
|---|---|---|---|
| Organism | rpfF homolog locus | Family | Known to produce DSF |
| *Cronobacter sakazakii* | WP_085344885 | Enterobacteriaceae | Yes |
| *Stenotrophomonas maltophilia* | WP_005416390 | Xanthomonadaceae | Yes |
| *Achromobacter xylosoxidans* | WP_054444565 | Alcaligenaceae | No |
| *Enterobacter cloacae* | WP_129362672 | Enterobacteriaceae | No |
| *Pantoea agglomerans* | WP_124890011 | Erwiniaceae | No |
| *Yersinia enterocolitica* | AKF40192 | Yersiniaceae | No |
| *Serratia marcescens* | WP_148874552 | Yersiniaceae | No |
| *Xylella fastidiosa* Temecula1 | AAO28287 | Xanthomonadaceae | Yes |
| *Xanthomonas campestris* pathovar *campestris* | AAM41146 | Xanthomonadaceae | Yes |
| *Burkholderia cenocepacia* | CAR54439 | Burkholderiaceae | Yes |
| *Cronobacter turicensis* | TWR33075 | Enterobacteriaceae | Yes |
| *Pseudomonas aeruginosa* | NP_249436 | Pseudomonadaceae | Yes |

TABLE 3

Protein sequence homology analysis between different RpfF homolog

| Organism | RpfF homolog locus | Reported to produce DSF | Amino acid SEQ ID NO | Construct tested | Amino Acid identity with *Xylella* RpfF | Amino Acid Similarity to *Xylella* RpfF |
|---|---|---|---|---|---|---|
| *Xylella fastidiosa* Temecula1 | AAO28287 | Yes | 1 | X | — | — |
| *Xanthomonas campestris* pathovar *campestris* | AAM41146 | Yes | 10 | X | 67% | 80% |
| *Stenotrophomonas maltophilia* | WP_005416390 | Yes | 13 | X | 48% | 67% |
| *Pseudomonas aeruginosa* | NP_249436 | Yes | 16 | X | 32% | 44% |
| *Cronobacter turicensis* | TWR33075 | Yes | 7 | X | 38% | 54% |
| *Burkholderia cenocepacia* | CAR54439 | Yes | 18 | X | 36% | 52% |
| *Yersinia enterocolitica* | AKF40192 | No | 19 | | 37% | 56% |
| *Serratia marcescens* | WP_148874552 | No | 20 | | 35% | 53% |
| *Pantoea agglomerans* | WP_124890011 | No | 21 | | 37% | 53% |
| *Enterobacter cloacae* | WP_129362672 | No | 24 | | 37% | 53% |
| *Cronobacter sakazakii* | WP_085344885 | No | 22 | | 39% | 54% |
| *Achromobacter xylosoxidans* | WP_054444565 | No | 23 | | 35% | 51% |

In some embodiment, the enzyme comprises an amino acid sequence that is at least 80%, at least 85%, at least 90%, at least 95%, at least 99% or more identical to SEQ ID NO: 20.

In some embodiment, the enzyme comprises an amino acid sequence that is at least 80%, at least 85%, at least 90%, at least 95%, at least 99% or more identical to SEQ ID NO: 21.

In some embodiment, the enzyme comprises an amino acid sequence that is at least 80%, at least 85%, at least 90%, at least 95%, at least 99% or more identical to SEQ ID NO: 22.

In some embodiment, the enzyme comprises an amino acid sequence that is at least 80%, at least 85%, at least 90%, at least 95%, at least 99% or more identical to SEQ ID NO: 23.

In some embodiment, the enzyme comprises an amino acid sequence that is at least 80%, at least 85%, at least 90%, at least 95%, at least 99% or more identical to SEQ ID NO: 24.

Genetically Engineered Bacterium

In one aspect, disclosed herein is a genetically engineered bacterium that comprises an exogenous nucleic acid encoding an enzyme that produces a diffusible signal factor (DSF), as described herein. As used herein, the term "genetically engineered" or "genetically modified" used in connection with a microorganism means that the microorganism comprises a genome that has been modified (relative to the original or natural-occurring genome of the microorganism), or comprises an exogenous introduced nucleic acid.

The recombinant bacteria disclosed herein,

- prevents *Salmonella* infection by disrupting an essential virulence function, rather than by killing or inhibiting the growth of the organism.
- is effective at very low concentrations (less than 1 μM in vitro).
- targets specifically *Salmonella*; unlikely to have deleterious effects on resident intestinal bacteria.
- produces compounds that eliminate the requirement for costly and time-consuming chemical synthesis.
- can be employed as a probiotic organism, administered to humans or non-human animals (e.g., sheep, turkeys, goats, dogs, cats, cattle, swine, chicken, ducks and other commercially-important domesticated animals) to prevent *Salmonella* carriage and disease.

In some embodiments, the exogenous nucleic acid comprises a gene that is codon-optimized for expression in a host genetically engineered bacterium (such as *E. coli* and *Salmonella*). In some embodiments, the exogenous nucleic acid is expressed in a bacterium, to produce DSFs. As used herein, the term "codon-optimized" refers to nucleic acid molecules that are modified based on the codon usage of the host species (e.g., a specific *E. coli, Salmonella* or probiotic bacterium species used), but without altering the polypeptide sequence encoded by the nucleic acid.

In some embodiments, the exogenous nucleic acid comprises a sequence that is at least 80%, at least 85%, at least 90%, at least 95%, at least 99% or more identical to a sequence selected from the group consisting of SEQ ID NOs: 2, 3, 4, 5, 6, 8, 9, 11, 12, 14, 15, and 17.

In some embodiments, the exogenous nucleic acid comprises a sequence that is at least 80%, at least 85%, at least 90%, at least 95%, at least 99% or more identical to SEQ ID NO: 2.

In some embodiments, the exogenous nucleic acid comprises a sequence that is at least 80%, at least 85%, at least 90%, at least 95%, at least 99% or more identical to SEQ ID NO: 3.

In some embodiments, the exogenous nucleic acid comprises a sequence that is at least 80%, at least 85%, at least 90%, at least 95%, at least 99% or more identical to SEQ ID NO: 4.

In some embodiments, the exogenous nucleic acid comprises a sequence that is at least 80%, at least 85%, at least 90%, at least 95%, at least 99% or more identical to SEQ ID NO: 5.

In some embodiments the exogenous nucleic acid comprises a sequence that is at least 80%, at least 85%, at least 90%, at least 95%, at least 99% or more identical to SEQ ID NO: 6.

In some embodiments, the exogenous nucleic acid comprises a sequence that is at least 80%, at least 85%, at least 90%, at least 95%, at least 99% or more identical to SEQ ID NO: 8.

In some embodiments, the vector comprises a nucleic acid sequence that is at least 80%, at least 85%, at least 90%, at least 95%, at least 99% or more identical to SEQ ID NO: 9.

In some embodiments, the exogenous nucleic acid comprises a sequence that is at least 80%, at least 85%, at least 90%, at least 95%, at least 99% or more identical to SEQ ID NO: 11.

In some embodiments, the exogenous nucleic acid comprises a sequence that is at least 80%, at least 85%, at least 90%, at least 95%, at least 99% or more identical to SEQ ID NO: 12.

In some embodiments, the exogenous nucleic acid comprises a sequence that is at least 80%, at least 85%, at least 90%, at least 95%, at least 99% or more identical to SEQ ID NO: 14.

In some embodiments, the exogenous nucleic acid comprises a sequence that is at least 80%, at least 85%, at least 90%, at least 95%, at least 99% or more identical to SEQ ID NO: 15.

In some embodiments, the exogenous nucleic acid comprises a sequence that is at least 80%, at least 85%, at least 90%, at least 95%, at least 99% or more identical to SEQ ID NO: 17.

In some embodiments, the exogenous nucleic acid encodes an amino acid sequence that is at least 80%, at least 85%, at least 90%, at least 95%, at least 99% or more identical to a sequence selected from the group consisting of SEQ ID NOs: 1, 7, 10, 13, 16, and 18-24.

In some embodiment, the exogenous nucleic acid encodes an amino acid sequence that is at least 80%, at least 85%, at least 90%, at least 95%, at least 99% or more identical to SEQ ID NO: 1.

In some embodiment, the exogenous nucleic acid encodes an amino acid sequence that is at least 80%, at least 85%, at least 90%, at least 95%, at least 99% or more identical to SEQ ID NO: 7.

In some embodiment, the exogenous nucleic acid encodes an amino acid sequence that is at least 80%, at least 85%, at least 90%, at least 95%, at least 99% or more identical to SEQ ID NO: 10.

In some embodiment, the exogenous nucleic acid encodes an amino acid sequence that is at least 80%, at least 85%, at least 90%, at least 95%, at least 99% or more identical to SEQ ID NO: 13.

In some embodiment, the exogenous nucleic acid encodes an amino acid sequence that is at least 80%, at least 85%, at least 90%, at least 95%, at least 99% or more identical to SEQ ID NO: 16.

In some embodiment, the exogenous nucleic acid encodes an amino acid sequence that is at least 80%, at least 85%, at least 90%, at least 95%, at least 99% or more identical to SEQ ID NO: 18.

In some embodiment, the exogenous nucleic acid encodes an amino acid sequence that is at least 80%, at least 85%, at least 90%, at least 95%, at least 99% or more identical to SEQ ID NO: 19.

In some embodiment, the exogenous nucleic acid encodes an amino acid sequence that is at least 80%, at least 85%, at least 90%, at least 95%, at least 99% or more identical to SEQ ID NO: 20.

In some embodiment, the exogenous nucleic acid encodes an amino acid sequence that is at least 80%, at least 85%, at least 90%, at least 95%, at least 99% or more identical to SEQ ID NO: 21.

In some embodiment, the exogenous nucleic acid encodes an amino acid sequence that is at least 80%, at least 85%, at least 90%, at least 95%, at least 99% or more identical to SEQ ID NO: 22.

In some embodiment, the exogenous nucleic acid encodes an amino acid sequence that is at least 80%, at least 85%, at least 90%, at least 95%, at least 99% or more identical to SEQ ID NO: 23.

In some embodiment, the exogenous nucleic acid encodes an amino acid sequence that is at least 80%, at least 85%, at least 90%, at least 95%, at least 99% or more identical to SEQ ID NO: 24.

In some embodiments, the exogenous nucleic acid further comprises a promoter. In some embodiments, the promoter is a native promoter. In some embodiments, the promoter is a heterologous promoter (i.e., the promoter is of a different origin as compared to the nucleic acid). In a specific embodiment, the native promoter is the promoter of the rpfF gene from *Xylella fastidiosa*. In some embodiments, the promoter is a constitutive promoter. In some embodiments, the promoter is an inducible promoter. In some embodiments the inducible promoter is selected from a tacI, a tacII and an araBAD promoter. tacI and tacII promoters are inducible with the chemical O-Nitrophenyl-β-D-galactopyranoside (ONPG). araBAD promoter is inducible with the sugar arabinose. In some embodiments, the inducible promoter is a lac operon, which can be induced by Isopropyl β-D-1-thiogalactopyranoside (IPTG).

In some embodiments, the exogenous nucleic acid is provided in a plasmid for introduction into a recipient bacteria strain. In some embodiments, the plasmid is pUC57. In some embodiments, plasmid vectors other than pUC57 are used to control production of cis-2 fatty acids. rpfF or homologs can be expressed from plasmids of differing copy number or stability to optimize production.

In some embodiments, the exogenous nucleic acid is integrated into the genome of a bacterium. Conventional methods of gene integration can be used to integrate these genes in single copy into the chromosome of the bacteria. Genomic integration is more advantageous than plasmid-based expression, as integrated constructs are stable and do not require antibiotic selection to be maintained. In a specific embodiment, the exogenous nucleic acid is integrated into the genome of *Salmonella*, thus creating strains of *Salmonella* deficient in virulence. In some embodiments, the exogenous nucleic is cloned into *Pantoea agglomerans* to produce several DSFs.

In some embodiments, the bacterium is a probiotic bacterium. In some embodiments, the probiotic bacterium is selected from genera *Escherichia, Propionibacterium, Lactobacillus, Bifidobacterium* and *Streptococcus*. In some embodiments, the probiotic bacterium is selected from *Escherichia coli* strain Nissle 1917, *Escherichia coli* strain MG1655, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*; and *Propionibacterium freudenreichii*. In a specific embodiment, the bacterium is *E. coli*. In a specific embodiment, the bacterium is a species of genera *Salmonella* or *Pantoea*.

Composition

Another aspect of this disclosure is directed to a composition, comprising a genetically engineered bacterium described herein. In some embodiments, the composition further comprises a pharmaceutically or veterinarily acceptable carrier.

For the purposes of this disclosure, "a pharmaceutically acceptable carrier" means any of the standard pharmaceutical carriers.

"Veterinarily acceptable carrier," as used herein, refers to a carrier medium that does not interfere with the effectiveness of the biological activity of the active ingredient, and is not toxic to the veterinary subject to whom it is administered.

Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

Some examples of pharmaceutically acceptable liquid carriers include alcohols (e.g., ethanol), glycols (e.g., propylene glycol and polyethylene glycols), polyols (e.g., glycerol), oils (e.g., mineral oil or a plant oil), paraffins, and aprotic polar solvents acceptable for introduction into a mammal (e.g., dimethyl sulfoxide or N-methyl-2-pyrrolidone) any of which may or may not include an aqueous component (e.g., at least, above, up to, or less than 10, 20, 30, 40, or 50 vol % water). Some examples of pharmaceutically acceptable gels include long-chain polyalkylene glycols and copolymers thereof (e.g., poloxamers), cellulosic and alkyl cellulosic substances (as described in, for example, U.S. Pat. No. 6,432,415), and carbomers. The pharmaceutically acceptable wax may be or contain, for example, carnauba wax, white wax, bees wax, glycerol monostearate, glycerol oleate, and/or paraffins, such as described in, for example, PCT International Publication WO2009/117130.

In specific embodiments, a pharmaceutically/veterinarily acceptable carrier is a dietary supplement or food. Examples of food that can be used to deliver a composition comprising recombinant bacterial spores include, but are not limited to, baby formula, yogurt, milk cheese, kefir, sauerkraut, and chocolate.

In a specific embodiment, the composition is an animal feed composition. In a specific embodiment, the composition is a food product for humans (e.g., yogurt, kefir or other probiotic-containing food product) or a nutritional supplement.

Another aspect of this disclosure is directed to preventatives for infection and carriage by non-typhoidal serovars of *Salmonella*. Compounds can be consumed by humans or be fed to livestock and poultry to prevent the colonization of the intestine by *Salmonella*. Recombinant bacteria such as *E. coli* producing cis-2 unsaturated fatty acids (DSFs) can be directly administered to animals or humans to prevent *Salmonella* infection.

Methods for Treating or Preventing *Salmonella* Infections

Another aspect of this disclosure is directed to a method for treating or preventing a *Salmonella* infection (e.g., a *Salmonella enterica* infection) comprising administering to a subject in need of treatment or prevention an effective amount of a genetically engineered bacterium, wherein the genetically engineered bacterium comprises an exogenous nucleic acid encoding an enzyme that produces a DSF.

As used herein, the term "effective amount" means the total amount of each active component of a pharmaceutical composition or method that is sufficient to show a meaningful patient benefit, i.e., treatment, healing, prevention of the relevant medical condition, amelioration of the symptoms, or an increase in rate of treatment, healing, prevention or amelioration of such conditions, or inhibition of the progression of the condition.

In the method, genetically engineered bacterium, typically in the form of a pharmaceutical composition, as described herein, is enterally administered to the subject. In some embodiments, the subject has already contracted *Salmonella* when the subject is administered the genetically engineered bacterium, in which case the method of treating functions to inhibit or prevent *Salmonella* invasion of the intestinal epithelium in the subject, thereby inhibiting or preventing infection of the subject by *Salmonella*. In other embodiments, the subject has not contracted *Salmonella* when the subject is administered the genetically engineered bacterium, in which case the method of treating functions as a preventative measure to inhibit or prevent *Salmonella* invasion in the subject, thereby preventing or inhibiting *Salmonella* infection, should the subject contract *Salmonella*.

In some embodiments, the genetically engineered bacterium is administered as a composition in a pharmaceutically or veterinarily-acceptable carrier, as described herein.

In some embodiments, an effective amount of a genetically engineered bacterium is $1\times10^1$, $1\times10^2$, $1\times10^1$, $1\times10^4$, $1\times10^5$, $1\times10^6$, $1\times10^7$, $1\times10^8$, $1\times10^9$ or more said genetically engineered bacterium or its spores.

In some embodiments, the subject is a mammal. In some embodiments, the subject is a human. In some embodiments, the subject is a non-human animal. In some embodiments, the non-human animal is a domesticated animal. In some embodiments, the domesticated animal is selected from a horse, a camel, a dog, a cat, a pig, a cow, a goat and a sheep.

Expression Vector

Another aspect of this disclosure is directed to a vector comprising a nucleic acid encoding an enzyme that capable of producing a DSF.

In some embodiments the vector comprises a nucleic acid that encodes an enzyme that is selected from the group consisting of an enzyme encoded by the AAO28287 (rpfF) locus of *Xylella fastidiosa*, and an enzyme encoded by the CAR54439 locus from *Burkholderia cenocepacia*, an enzyme encoded by the TWR33075 locus of *Cronobacter turicensis*, an enzyme encoded by the WP_129362672 locus of *Enterobacter cloacae*, an enzyme encoded by the NP_249436 locus of *Pseudomonas aeruginosa*, an enzyme encoded by the WP_005416390 locus of *Stenotrophomonas maltophilia*, an enzyme encoded by the AAM41146 locus of *Xanthomonas campestris* pathovar *campestris*, an enzyme encoded by the WP_054444565 locus of *Achromobacter xylosoxidans*, an enzyme encoded by the WP_085344885 locus of *Cronobacter sakazakii*, an enzyme encoded by the WP_124890011 locus of *Pantoea agglomerans*, an enzyme encoded by the WP_148874552 locus of *Serratia marcescens*, and an enzyme encoded by the AKF40192 locus of *Yersinia enterocolitica*.

In some embodiment, the vector comprises a nucleic acid that encodes an amino acid sequence that is at least 80%, at least 85%, at least 90%, at least 95%, at least 99% or more identical to a sequence selected from SEQ ID NOs: 1, 7, 10, 13, 16.

In some embodiment, the vector comprises a nucleic acid that encodes an amino acid sequence that is at least 80%, at least 85%, at least 90%, at least 95%, at least 99% or more identical to SEQ ID NO: 1.

In some embodiment, the vector comprises a nucleic acid that encodes an amino acid sequence that is at least 80%, at least 85%, at least 90%, at least 95%, at least 99% or more identical to SEQ ID NO: 7.

In some embodiment, the vector comprises a nucleic acid that encodes an amino acid sequence that is at least 80%, at least 85%, at least 90%, at least 95%, at least 99% or more identical to SEQ ID NO: 10.

In some embodiment, the vector comprises a nucleic acid that encodes an amino acid sequence that is at least 80%, at least 85%, at least 90%, at least 95%, at least 99% or more identical to SEQ ID NO: 13.

In some embodiment, the vector comprises a nucleic acid that encodes an amino acid sequence that is at least 80%, at least 85%, at least 90%, at least 95%, at least 99% or more identical to SEQ ID NO: 16.

In some embodiment, the vector comprises a nucleic acid that encodes an amino acid sequence that is at least 80%, at least 85%, at least 90%, at least 95%, at least 99% or more identical to SEQ ID NO: 18.

In some embodiment, the vector comprises a nucleic acid that encodes an amino acid sequence that is at least 80%, at least 85%, at least 90%, at least 95%, at least 99% or more identical to SEQ ID NO: 19.

In some embodiment, the vector comprises a nucleic acid that encodes an amino acid sequence that is at least 80%, at least 85%, at least 90%, at least 95%, at least 99% or more identical to SEQ ID NO: 20.

In some embodiment, the vector comprises a nucleic acid that encodes an amino acid sequence that is at least 80%, at least 85%, at least 90%, at least 95%, at least 99% or more identical to SEQ ID NO: 21.

In some embodiment, the vector comprises a nucleic acid that encodes an amino acid sequence that is at least 80%, at least 85%, at least 90%, at least 95%, at least 99% or more identical to SEQ ID NO: 22.

In some embodiment, the vector comprises a nucleic acid that encodes an amino acid sequence that is at least 80%, at least 85%, at least 90%, at least 95%, at least 99% or more identical to SEQ ID NO: 23.

In some embodiment, the vector comprises a nucleic acid that encodes an amino acid sequence that is at least 80%, at least 85%, at least 90%, at least 95%, at least 99% or more identical to SEQ ID NO: 24.

In some embodiments, the vector comprises a nucleic acid sequence that is at least 80%, at least 85%, at least 90%, at least 95%, at least 99% or more identical to a sequence selected from the group consisting of SEQ ID NOs: 2, 3, 4, 5, 6, 8, 9, 11, 12, 14, 15, and 17.

In some embodiments, the vector comprises a nucleic acid sequence that is at least 80%, at least 85%, at least 90%, at least 95%, at least 99% or more identical to SEQ ID NO: 2.

In some embodiments, the vector comprises a nucleic acid sequence that is at least 80%, at least 85%, at least 90%, at least 95%, at least 99% or more identical to SEQ ID NO: 3.

In some embodiments, the vector comprises a nucleic acid sequence that is at least 80%, at least 85%, at least 90%, at least 95%, at least 99% or more identical to SEQ ID NO: 4.

In some embodiments, the vector comprises a nucleic acid sequence that is at least 80%, at least 85%, at least 90%, at least 95%, at least 99% or more identical to SEQ ID NO: 5.

In some embodiments, the vector comprises a nucleic acid sequence that is at least 80%, at least 85%, at least 90%, at least 95%, at least 99% or more identical to SEQ ID NO: 6.

In some embodiments, the vector comprises a nucleic acid sequence that is at least 80%, at least 85%, at least 90%, at least 95%, at least 99% or more identical to SEQ ID NO: 8.

In some embodiments, the vector comprises a nucleic acid sequence that is at least 80%, at least 85%, at least 90%, at least 95%, at least 99% or more identical to SEQ ID NO: 9.

In some embodiments, the vector comprises a nucleic acid sequence that is at least 80%, at least 85%, at least 90%, at least 95%, at least 99% or more identical to SEQ ID NO: 11.

In some embodiments, the vector comprises a nucleic acid sequence that is at least 80%, at least 85%, at least 90%, at least 95%, at least 99% or more identical to SEQ ID NO: 12.

In some embodiments, the vector comprises a nucleic acid sequence that is at least 80%, at least 85%, at least 90%, at least 95%, at least 99% or more identical to SEQ ID NO: 14.

In some embodiments, the vector comprises a nucleic acid sequence that is at least 80%, at least 85%, at least 90%, at least 95%, at least 99% or more identical to SEQ ID NO: 15.

In some embodiments, the vector comprises a nucleic acid sequence that is at least 80%, at least 85%, at least 90%, at least 95%, at least 99% or more identical to SEQ ID NO: 17.

In some embodiments, the vector comprises a nucleic acid sequence that is codon optimized based on the codon usage of a host species (e.g., a specific *E. coli, Salmonella* or probiotic bacterium species), but without altering the polypeptide sequence encoded by the nucleic acid sequence.

Methods of Producing DSFs

Another aspect of this disclosure is directed to a method of producing a diffusible signal factor (DSF), comprising culturing a genetically engineered bacterium described herein (which comprises an exogenous nucleic acid encoding an enzyme that produces a DSF) under conditions that allow the genetically engineered bacterium to express the enzyme that produces a DSF, thereby producing the DSF. In some embodiment, the method further comprises purifying the produced DSF from the cell culture.

In some embodiments, DSFs are produced in a probiotic bacterial strain. In some embodiments, the probiotic strain is selected from genera *Escherichia, Propionibacterium, Lactobacillus, Bifidobacterium* and *Streptococcus*. In some embodiments, the probiotic strain is selected from *Escherichia coli* strain Nissle 1917, *Escherichia coli* strain MG1655, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*; and *Propionibacterium freudenreichii*. In a specific embodiment, the probiotic strain is a strain of E. co/i. In a specific embodiment, rpfF or its homologs are expressed in *E. coli* strains known to colonize the intestine of animals, including the recognized probiotic stain Nissle 1917.

In some embodiments, DSFs are produced from a species of *Salmonella* or *Pantoea*.

EXAMPLES

Example 1: Materials and Methods rpfF Constructs and Recombinant Strains

The rpfF gene of *Xylella fastidiosa* and the BCAM0581 gene of *Burkholderia cenocepacia* were modified to optimize expression in *E. coli* by altering their codons to those most frequently used in E. co/i. Each was fused to a modified tac promoter lacking the lac operator region and with a consensus ribosome-binding site to create a constitutive promoter. Constructs were generated and cloned onto the EcoRV restriction enzyme site of plasmid pUC57 by a commercial source. The plasmid constructs were introduced by transformation into the K12 strain of *E. coli* MG1655, and into *Salmonella* serovar *Typhimurium* strain ATCC 14028s. These recombinant strains were grown in co-culture with a strain derived from *Salmonella* serovar *Typhimurium* strain ATCC 14028s that harbors a plasmid carrying a fusion of the invasion gene hilA to the luxCDABE reporter. The ability of recombinant strains to repress hilA expression in the co-cultured strain was assessed by reduction in light production from the luxCDABE genes. The specific compound produced was determined by gas chromatography.

Sequences

- SEQ ID NO: 1*: Xylella fastidiosa* Temecula1 rpfF amino acid sequence.
- SEQ ID NO: 2*: Xylella fastidiosa* Temecula1 rpfF gene nucleotide sequence.
- SEQ ID NO: 3: Codon-optimized nucleotide sequence of rpfF from *Xylella fastidiosa.*
- Position 1-68: constitutive promoter based upon the tac promoter. Position 69-941: rpfF open reading frame (ORF). Position 942-947: BglII cloning site
- SEQ ID NO: 4: Codon-optimized nucleotide sequence (version 2) of rpfF from *Xylella fastidiosa*. Position 1-82: tacI promoter. Position 83-955: ORF. Position 956-961: BglII cloning site.
- SEQ ID NO: 5: Codon-optimized nucleotide sequence (version 3) of rpfF of *Xylella fastidiosa.*
- SEQ ID NO: 6: rpfF homolog gene nucleotide sequence in *Cronobacter turicensis* strain MOD1_Md1sN.
- SEQ ID NO: 7*: Cronobacter turicensis* rpfF homolog amino acid sequence.
- SEQ ID NO: 8: rpfF homolog gene nucleotide sequence in *Xanthomonas campestris* pv. *campestris.*
- SEQ ID NO: 9: Codon-optimized nucleotide sequence of rpfF homolog of *Xanthomonas campestris* pv. *campestris.*
- SEQ ID NO: 10: *Xanthomonas campestris* pv. *campestris* rpfF homolog amino acid sequence.
- SEQ ID NO: 11: rpfF homolog gene nucleotide sequence in *Stenotrophomonas maltophilia* K279a.
- SEQ ID NO: 12: Codon-optimized nucleotide sequence of rpfF homolog of *Stenotrophomonas maltophilia* K279a.
- SEQ ID NO: 13: *Stenotrophomonas maltophilia* rpfF homolog amino acid sequence.
- SEQ ID NO: 14: rpfF homolog gene nucleotide sequence in *Pseudomonas aeruginosa.*
- SEQ ID NO: 15: Codon-optimized nucleotide sequence of rpfF homolog in *Pseudomonas aeruginosa.*
- SEQ ID NO: 16: *Pseudomonas aeruginosa* rpfF homolog amino acid sequence.
- SEQ ID NO: 17: rpfF homolog gene nucleotide sequence in *Enterobacter cloacae* subsp. *cloacae* (ATCC 13047).
- SEQ ID NO: 18: *Burkholderia cenocepacia* rpfF homolog amino acid sequence.
- SEQ ID NO: 19: *Yersinia enterocolitica* rpfF homolog amino acid sequence.
- SEQ ID NO: 20: *Serratia marcescens* rpfF homolog amino acid sequence.
- SEQ ID NO: 21: *Pantoea agglomerans* rpfF homolog amino acid sequence.
- SEQ ID NO: 22*: Cronobacter sakazakii* rpfF homolog amino acid sequence.
- SEQ ID NO: 23: *Achromobacter xylosoxidans* rpfF homolog amino acid sequence.
- SEQ ID NO: 24: *Enterobacter cloacae* subsp. *cloacae* rpfF homolog amino acid sequence.

Cloning and Expression of Cis-2Fatty Acid Production Genes

Figure 7:
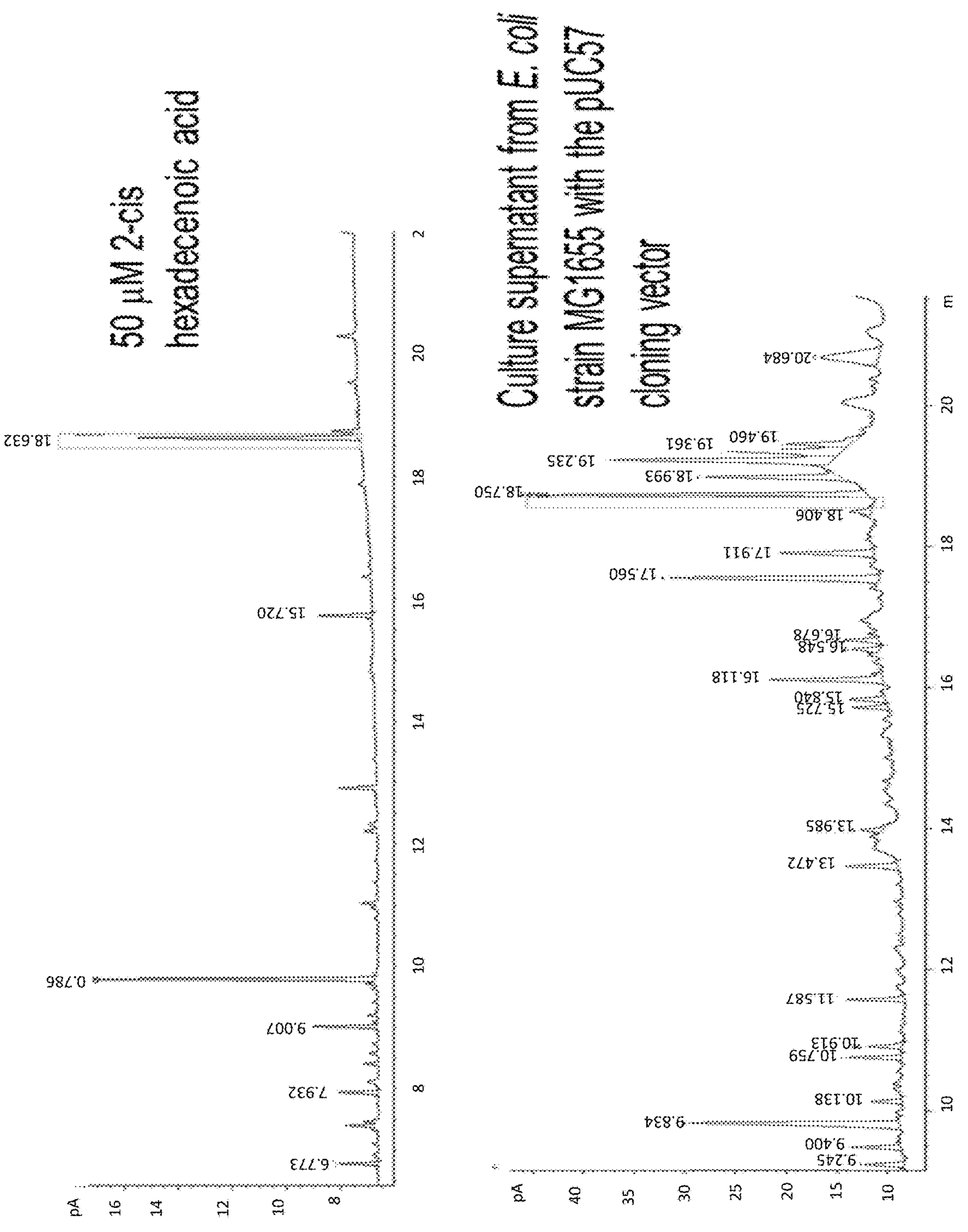
FIG. 7. Gas chromatography results. The expression of rpfF produced a peak of the appropriate retention time to be 2-cis-hexadecenoic acid. This peak was absent in the control sample (*E. coli* with the pUC57 plasmid). It was also absent in the strain expressing BCAM0581.
Figure 7:
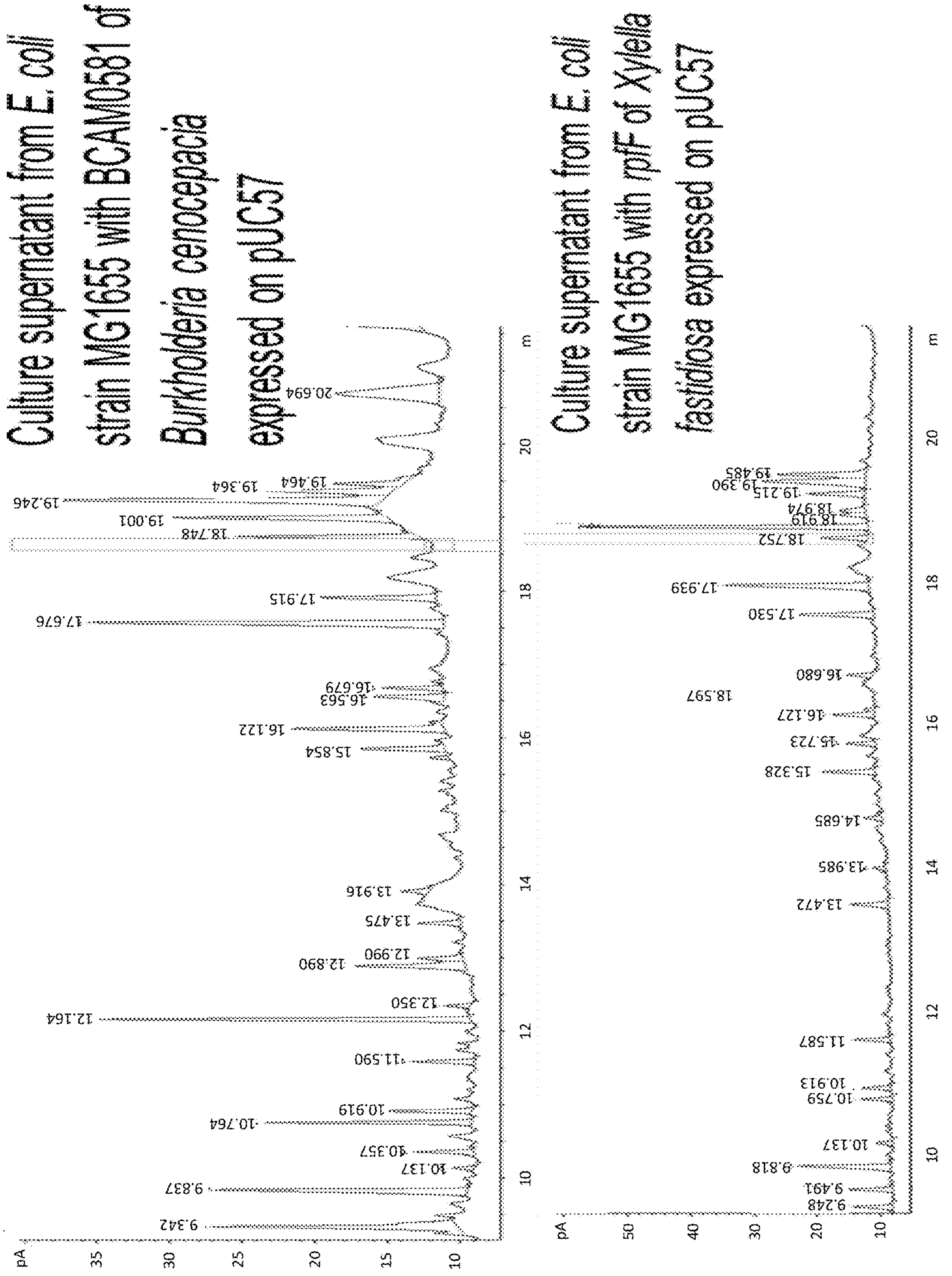

Genes termed BCAM0581 in *Burkholderia cenocepacia* and rpfF in *Xylella fastidiosa* encode homologous enoyl-CoA hydratase proteins that introduce a cis-2 double bond into long-chain fatty acids, producing a diffusible signal factor. In *Burkholderia cenocepacia* the primary product is cis-2-dodecenoic acid, while in *Xylella fastidiosa* they are 2-cis-hexadecenoic and 2-cis-tetradecenoic acids. The inventors codon-optimized these two genes for expression in *E. coli* and expressed each under the control of a constitutive promoter as constructs cloned into the EcoRV site of the pUC57 plasmid. The inventors then used gas chromatography (GC) to assess the presence of 2-cis-hexadecenoic acid in culture supernatants by comparing it to a commercially obtained preparation of this chemical (FIG. 7). The expression of rpfF produced a peak of the appropriate retention time to be 2-cis-hexadecenoic acid. This peak was absent in the control sample (*E. coli* with the pUC57 plasmid). It was also absent in the strain expressing BCAM0581.

Figure 5:
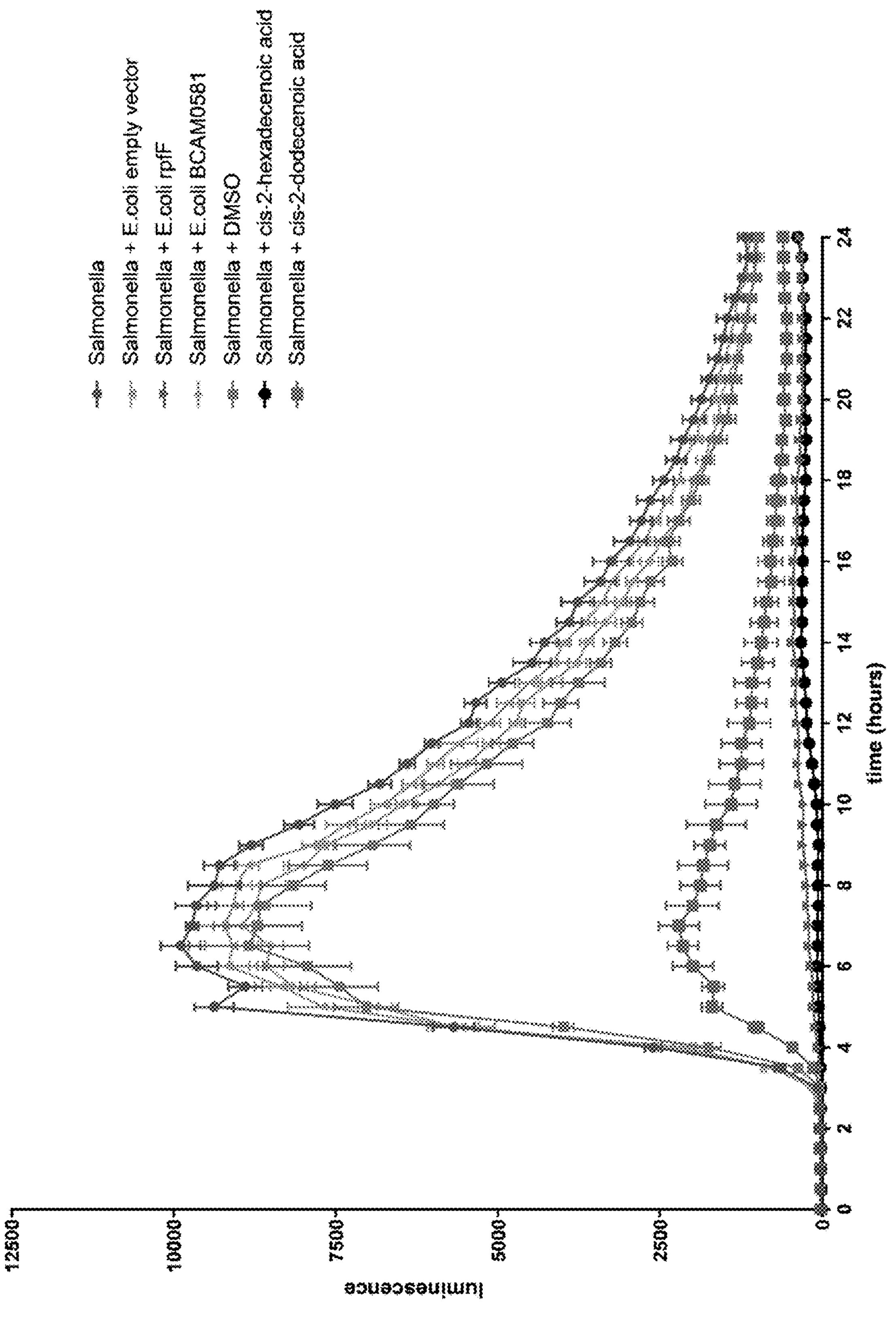
FIG. 5. Invasion gene expression in *Salmonella* is greatly reduced when co-cultured with *E. coli* recombinantly expressing rpfF of *Xylella fastidiosa*. A *Salmonella Typhimurium* strain carrying a hilA-lux reporter fusion was co-cultured with *E. coli* expressing DSF-production genes. HilA is a central regulator of invasion and is required for virulence. *E. coli* expressing rpfF (purple triangles) repressed hilA expression to a level similar to that using 2.5 μM 2-cis-hexadecenoic acid in the culture medium (black circles). 2-cis-hexadecenoic acid (brown squares) reduced expression to a lesser degree, but BCAM0581 (yellow diamonds), predicted to produce 2-cis-dodecenoic acid, did not repress.
Figure 6:
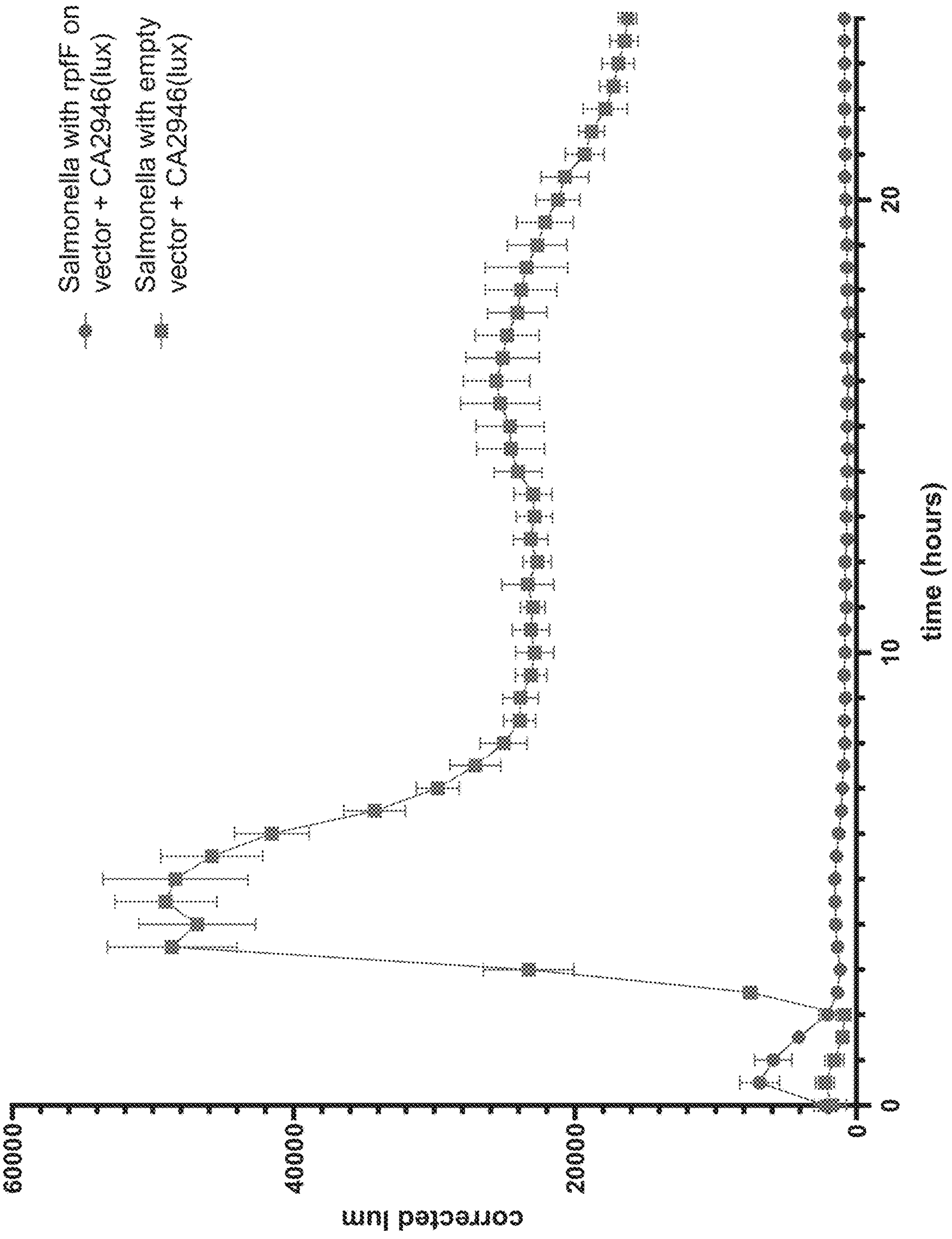
FIG. 6. Invasion gene expression in *Salmonella* is greatly reduced when co-cultured with *Salmonella* recombinantly expressing rpfF of *Xylella fastidiosa*. A *Salmonella Typhimurium* strain carrying a hilA-lux reporter fusion was co-cultured with an S. *Typhimurium* strain expressing rpfF (blue circles) or with the control vector (red squares).

To assess the functional significance of recombinant enoyl-CoA hydratase expression, a *Salmonella Typhimurium* strain carrying a hilA-lux reporter fusion was co-cultured with *E. coli* expressing BCAM0581 or rpfF (FIG. 5). HilA is a central regulator of invasion and is required for virulence. *E. coli* expressing rpfF (purple triangles) repressed hilA expression to a level similar to that using 2.5 μM 2-cis-hexadecenoic acid in the culture medium (black circles). 2-cis-dodecenoic acid (brown squares) reduced expression to a lesser degree, but BCAM0581 (yellow diamonds), predicted to produce 2-cis-dodecenoic acid, did not repress.

A single gene, rpfF of *Xylella fastidiosa*, is sufficient to produce a DSF of the 2-cis fatty-acid class in Enterobacteriaceae. Codon-optimized rpfF expression by either *E. coli* or *Salmonella* produces a diffusible signal that can be sensed by neighboring bacteria. Expression of rpfF by *E. coli* or *Salmonella* reduces *Salmonella* invasion gene expression. In some embodiments, the rpfF gene (or a homolog thereof, e.g., a gene listed in Table 1) is integrated into the genome of probiotic bacterial strains to assess the effects on *Salmonella* invasion.

Electro Mobility Shift Assays (EMSAs)

Electrophoretic mobility shift assays (EMSAs). EMSAs were performed as previously described (Y. A. Golubeva et al., *MBio,* 7(1), 2016). Briefly, 10 nM of hilA promoter DNA was mixed with 150 μM HilD, HilC or RtsA in a binding buffer containing 20 mM KCl, 1% glycerol, 1 mM DTT, 0.04 mM EDTA, 0.05% Tergitol™ NP-40 and 20 mM HEPES, pH 7.3. cis-2-hexadecenoic acid was tested at concentrations of 1 to 200 μM. Binding was performed at room temperature for 20 minutes. Samples were separated on 6% Novex® TBE DNA retardation gels, and DNA was stained using SYBR® green (Invitrogen).

Figure 8:
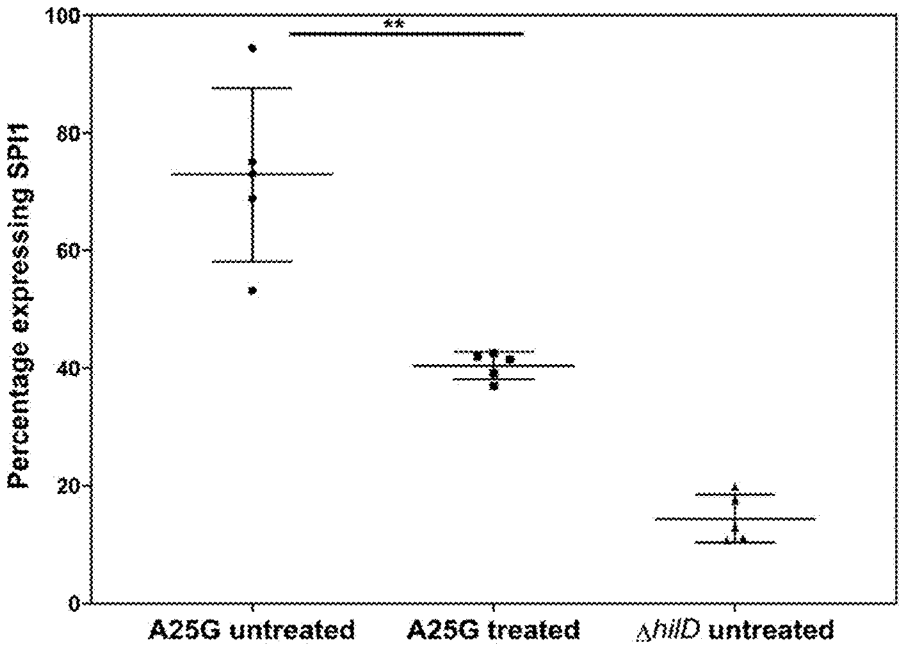
FIG. 8. Data showing that cis-2-hexadecenoic acid reduces the percentage of *Salmonella* expressing SPI in the gut. Three groups of mice (n=5/group) were inoculated with *Salmonella* strains carrying phoN::BFP (for identifying *Salmonella*) and sicA→GFP (for monitoring SPI expression), with either a hilD UTR A25G mutation or a hilD null mutation as shown in the graph. Percentage SPI1 expression was calculated as the portion of BFP-expressing bacteria that also expressed GFP. Data are presented as percentages with means shown by the horizontal lines and the error bars denoting standard deviations. Asterisks denote expression levels significantly different from the control (**–P<0.01).

Example 2: 2-Cis-Hexadecenoic Acid Reduces the Percentage of *Salmonella* Expressing an Invasion Gene in the Gut The ability of orally administered 2-cis-hexadecenoic acid to inhibit *Salmonella* invasion-gene expression in the complex chemical environment of the gut was determined. Only a portion of bacteria activate invasion genes in the gut. To improve the sensitivity of the assay, the inventors used a strain carrying a hilD UTR A25 to a G single base mutation, resulting in increased invasion-gene expression due to altered mRNA stability. This strain additionally carried a constitutively expressed AphoN::BFP construct for *Salmonella* identification, and a sicA-GFP reporter fusion to monitor SPI1 expression. The administration of 2-cis-hexadecenoic acid to mice at 1.5 mM in drinking water significantly reduced the percentage of bacteria expressing an invasion gene in the caecum by 2-fold. The proportion of a ΔhilD null mutant expressing the invasion gene was 5-fold lower than the untreated A25G strain, indicating the importance of HilD for invasion activation in the gut. As fatty acids are rapidly absorbed in the upper gastrointestinal tract, it is presumed that low amounts of 2-cis-hexadecenoic acid were available in the caecum. Compared to the in vitro potency of 2-cis-hexadecenoic acid, an estimated concentration of between 2.5 μM and 10 μM would repress invasion to the percentage observed in the caecum. These results demonstrate that the DSF 2-cis-hexadecenoic acid can signal to inhibit invasion gene expression in the gut (FIG. 8).

Example 3: 2-Cis-Unsaturated Fatty Acids Destabilize HilD

Figure 9:
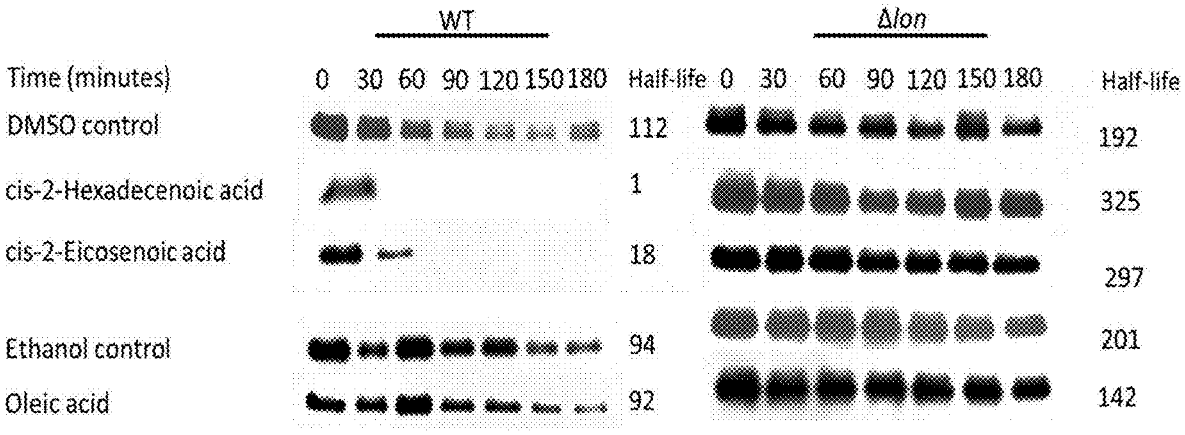
FIG. 9. Data showing cis-2-unsaturated fatty acids inactivate HilD with consequent degradation by Lon. Western blot data showing that cis-2-unsaturated fatty acids reduce HilD half-life in the presence of Lon. Strains carrying a hilD-3×FLAG construct under the control of a tetracycline-inducible promoter, with Lon present or absent, were grown in the presence of 20 μM cis-2-unsaturated fatty acids. HilD half-life was determined by western blotting for 3×FLAG.

The effects of DSFs on HilD protein stability were assessed. See FIG. 9. A strain carrying hilD under a tetracycline-controlled promoter and a C-terminal 3×FLAG tag was used to measure the stability of HilD. The half-life of HilD from bacteria grown in the absence of DSFs was 112 minutes, but addition of 2-cis-hexadecenoic acid to the culture drastically reduced that half-life, to 1 minute. cis-2-eicosenoic acid reduced HilD half-life by a lesser extent, to 18 minutes, and oleic acid did so to 92 minutes. These data indicate that DSFs destabilize HilD. Lon protease is known to be responsible for HilD degradation, but genetic approaches indicated that lon was not required for the repressive effects of the 2-cis-hexadecenoic acid. The inventors therefore tested the role of Lon by assessing HilD protein half-life in a lon mutant. In the absence of lon, HilD protein accumulated, and the DSF had no effect on its stability. However, the DSF continued to repress hilA expression even in the absence of lon. It is therefore likely that DSFs inactivate HilD with consequent degradation by Lon, but that Lon plays no direct role in the repression of invasion genes by DSFs.

Figure 10:
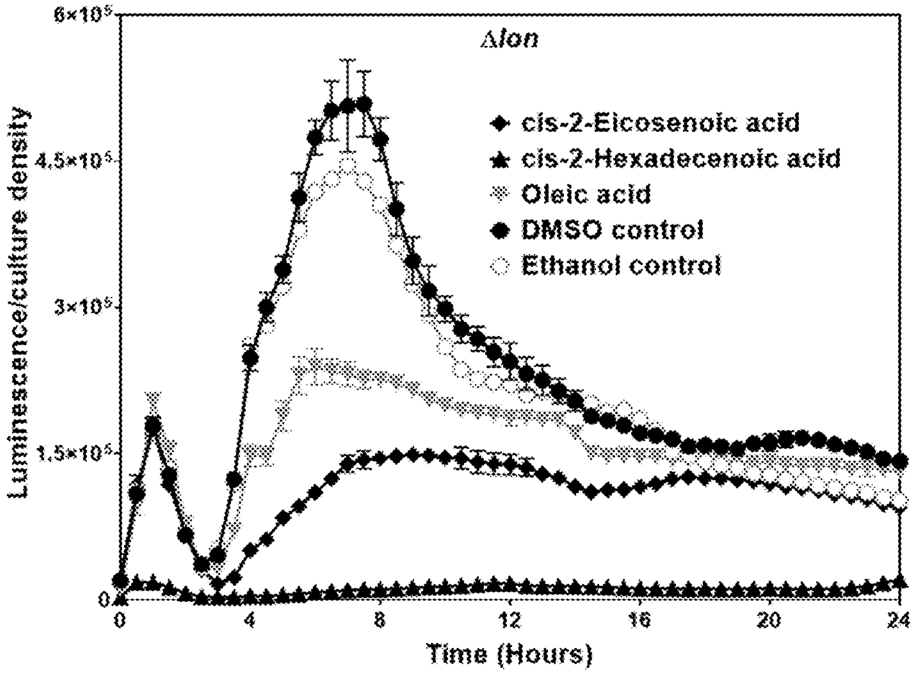
FIG. 10. Data showing that cis-2-unsaturated fatty acids repress hilA expression in the absence of Lon. A strain carrying a hilA::lux reporter fusion with a Δlon mutation was grown in the presence of 20 μM of the fatty acids. Expression of hilA is presented as luminescence normalized to bacterial culture density. The control culture contained the vehicle only (DMSO for cis-2-hexadecenoic acid and cis-2-eicosenoic acid, and ethanol for oleic acid) at identical concentration to the treated culture.
Figure 11:
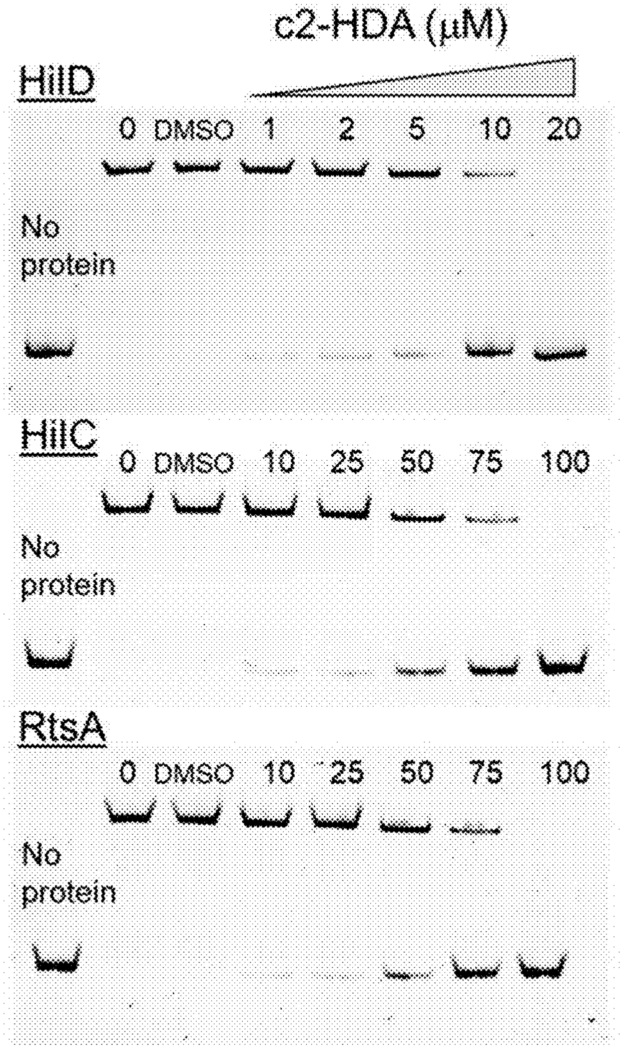
FIG. 11. Data showing that cis-2-hexadecenoic acid inhibits HilD, HilC and RtsA from binding their DNA target. In the presence of 20 μM fatty acid, HilD was completely inhibited from binding hilA promoter DNA, while concentrations of 1, 2, 5 and 10 μM did so partially. For HilC and RtsA, 100 μM cis-2-hexadecenoic acid prevented binding to the hilA promoter, while concentrations of 10, 25, 50 and 75 μM did so partially. All wells contained 10 nM of hilA promoter DNA. The indicated lanes contained 150 μM of protein.
Figures 12A, 12B, 12C:
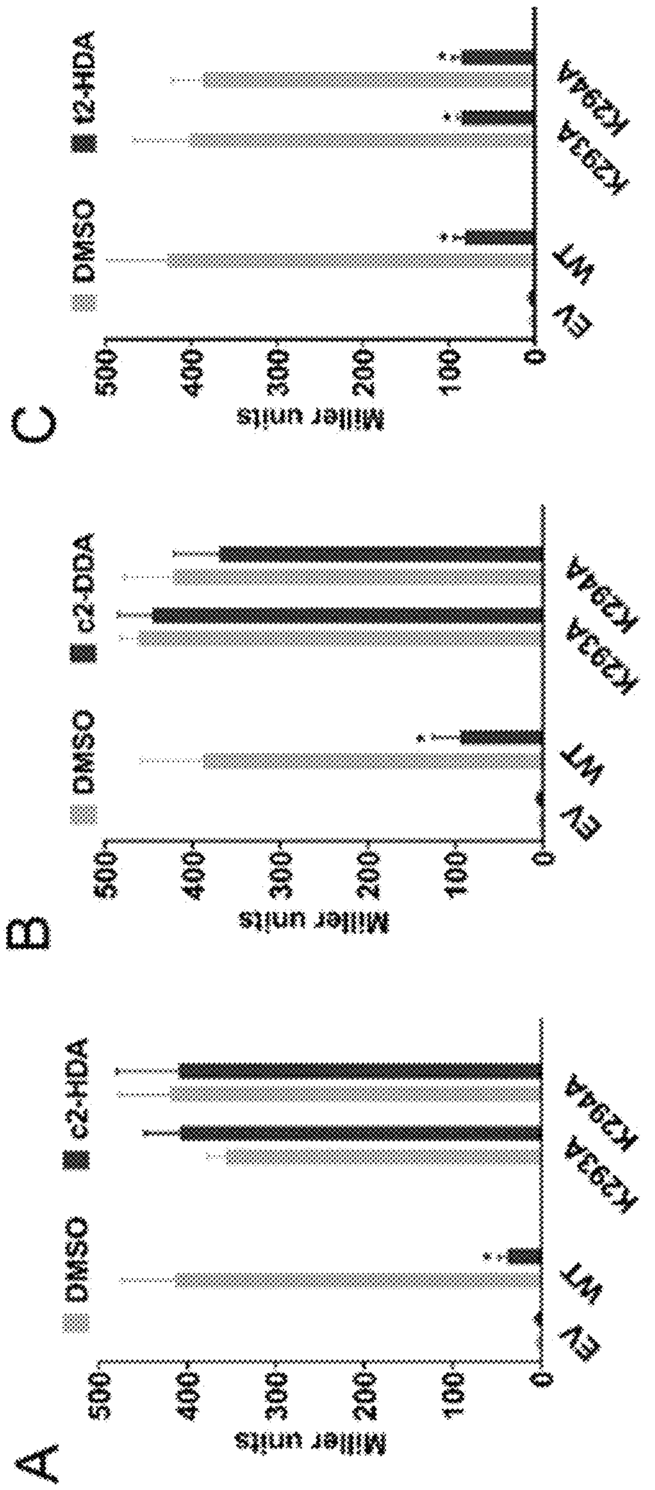
FIGS. 12A-12C. Data showing that specific amino acid residues of HilD are essential for repression by 2-cis-unsaturated DSFs. A-C. *Salmonella* strains expressing empty vector (EV) or wild type (WT) or mutant HilD were grown in the presence of 20 μM 2-cis-hexadecenoic acid (c2-HDA; A), 2-cis-dodecenoic acid (c2-DDA; B), or 2-trans-hexadecenoic acid (t2-HAD; C) and expression of the invasion gene sipB was measured using a lacZY transcriptional reporter fusion, by β-galactosidase assays. Bars represent mean±SD (n=4). Differences between respective DMSO controls and fatty acid treatments were calculated by Mann-Whitney test, * p<0.05.

Example 4: Cis-2-Unsaturated Fatty Acids Inhibit HilD, HilC and RtsA From Binding Their Target DNA The results presented in FIG. 10 indicate that cis-2-unsaturated fatty acids repressed HilD through an inactivation mechanism followed by protein degradation. It is hypothesized that these compounds directly interact with HilD, thus impairing its function. HilD binds to the hilA promoter (I. N. Olekhnovich et al., J. Bacteriol., 184(15), 4148-4160, 2002). The present research examined the effects of cis-2-unsaturated compounds on the binding of purified HilD to the hilA promoter using electrophoretic mobility shift assays (EMSA). In the absence of DSF, the expected binding of HilD to the hilA promoter was demonstrated by the retarded migration of this DNA fragment through the polyacrylamide gel (FIG. 7). Addition of 20 μM 2-cis-hexadecenoic acid, however, prevented the binding of HilD to the hilA promoter, whereas concentrations of 1, 2, 5, and 10 μM partially inhibited binding. HilC and RtsA also bind to the hilA promoter and induce expression of hilA. Addition of 100 μM 2-cis-hexadecenoic acid preventing binding of each of these two proteins to the hilA promoter, while concentrations of 10, 25, 50 and 75 μM partially inhibited binding. Therefore, the cis-2-unsaturated fatty acids directly inhibit the ability of HilD, HilC and RtsA to interact with their DNA target.

Example 5: Specific Amino Acid Residues of HilD are Essential for Repression by 2-Cis-Unsaturated DSFs The inventors used in silico methods to visualize the interaction of 2-cis-hexadecenoic acid with HilD. In the absence of an established structure of HilD, the X-ray crystal of its structural and functional homolog, ToxT of *Vibrio cholerae*, was used to create a virtual HilD replica by homology modeling. Virtual docking of 2-cis-hexadecenoic acid onto this HilD model found two amino acid residues (K293 and K294) whose side-chains were predicted to be in close proximity to the ligand. To test these predictions, each was replaced with an alanine, expressing the mutant constructs on a low copy-number plasmid. To isolate the effects of the hilD mutations from other invasion activators, these constructs were introduced into a *Salmonella* strain with null mutations in chromosomal hilC, rtsA, and hilD, thus eliminating all components of the invasion feed-forward regulatory loop. Using sipB::lacZY, a representative HilD-regulated gene, as a reporter, invasion-gene expression in cultures grown with 20 μM 2-cis-hexadecenoic acid was examined. The hilD mutants retained their full capacity to induce sipB in the absence of 2-cis-hexadecenoic acid, complementing the chromosomal hilD null mutant, and demonstrating that the point mutations did not reduce transcriptional activation by HilD. HilD mutants K293A and K294A were resistant to the repressive effects of 2-cis-hexadecenoic acid. No significant repression of sipB was observed in these mutants, compared to almost 11-fold reduction in the strain with a wild type HilD. The effect of disrupting residues K293 and K294 on invasion gene expression was specific only to LCFAs with a cis-2 unsaturation. The LCFA 2-cis-dodecenoic acid (c2-DDA), which reduced sipB expression by 4.1-fold in the wild type HilD strain, produced no significant reduction in the K293A and K294A mutants. Conversely, 2-trans-hexadecenoic acid (t2-HDA), which differs from 2-cis-hexadecenoic acid only in the spatial orientation of unsaturation at the second carbon, repressed sipB expression in mutant K293A (4.7-fold) and mutant K294A (4.5-fold) as well as wild type HilD (5.2-fold). These results thus identify the amino acids of HilD important for invasion gene repression by the 2-cis class of fatty acids.

Figure 13:
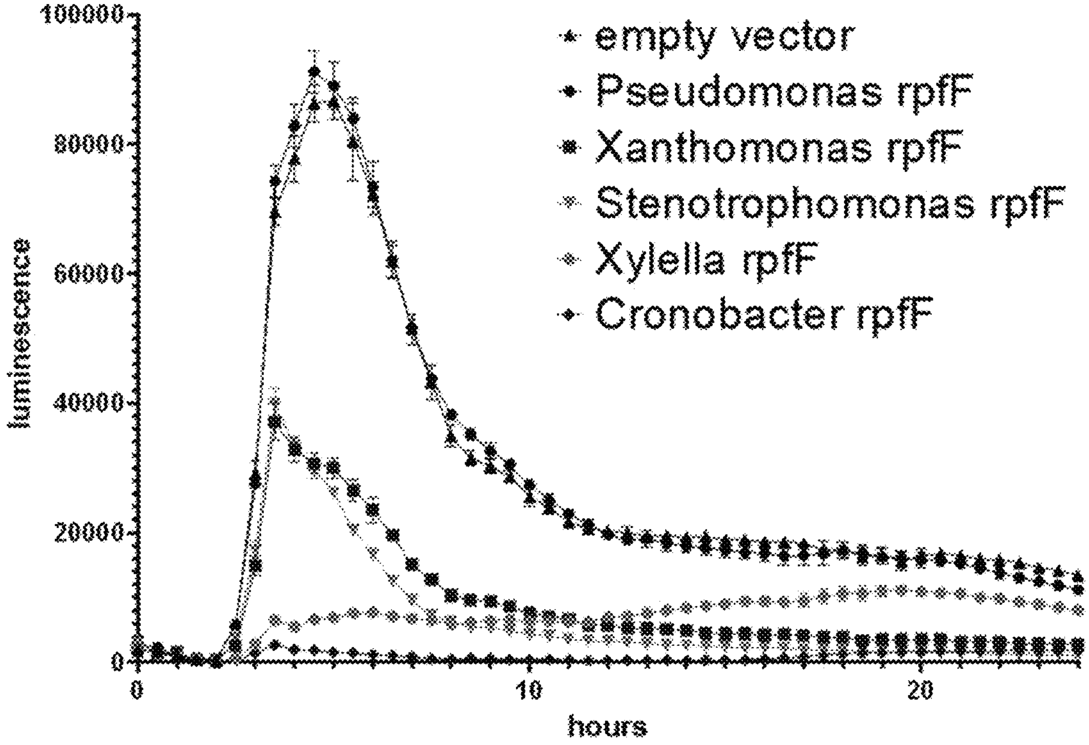
FIG. 13. Data showing that recombinant expression of rpfF by *E. coli* reduces *Salmonella* invasion gene expression in co-culture. Codon-optimized rpfF from the listed genera expressed on pUC57 in *E. coli* DH5α was grown in co-culture with *Salmonella* (1:10 *E. coli* to *Salmonella*), and hilA-luxCDABE repression was measured.

Example 6: Recombinant Expression of rpfF by *E. coli* Reduces *Salmonella* Invasion Gene Expression in Co-Culture Variants of rpfF found in several bacterial species encode homologous proteins with enoyl-CoA dehydratase and thioesterase activities that introduce a cis-2 double bond into long-chain fatty acids, generating diffusible signal factors. The inventors codon-optimized five of these genes for expression in *E. coli* K-12 (from the genera *Pseudomonas, Xanthomonas, Stenotrophomonas, Cronobacter* and *Xylella*) and expressed each under the control of a constitutive promoter as constructs cloned into the pUC57 plasmid. To assess the functional significance of recombinant RpfF production, a S. *Typhimurium* strain carrying a hilA-luxCDABE reporter fusion was co-cultured with *E. coli* expressing each construct (FIG. 13). As a stringent test of function, the *Salmonella* outnumbered the recombinant *E. coli* by 10 to 1. The RpfF homologs repressed the hilA reporter expression to varying degrees, with those from *Cronobacter* and *Xylella* being the most potent. The observed repression was equivalent to addition of high concentrations of 2-cis-hexadecenoic acid (1-2 μM) directly to growth media. These findings (shown in FIG. 13) thus demonstrate that the expression of a single gene, rpfF, in *E. coli* is necessary and sufficient to produce adequate 2-cis-hexadecenoic acid that can be secreted to inhibit the expression of invasion genes among neighboring *Salmonella* present in excess.

What is claimed is:

1. A genetically engineered bacterium, wherein the genetically engineered bacterium comprises an exogenous nucleic acid encoding an enzyme that introduces a cis-2 double bond to a fatty acid, thereby producing a diffusible signal factor (DSF), wherein the nucleic acid encoding the enzyme is codon-optimized for expression in the genetically engineered bacterium, and wherein the genetically engineered bacterium is a probiotic bacterium, wherein the probiotic bacterium is selected from the group consisting of genera *Escherichia, Propionibacterium, Lactobacillus, Bifidobacterium*, and *Streptococcus.*

2. The genetically engineered bacterium of claim 1, wherein a) the enzyme is selected from the group consisting of an enzyme encoded by the rpfF locus of *Xylella fastidiosa* comprising the nucleotide sequence of SEQ ID NO: 2, 3, 4 or 5, an enzyme encoded by the rpfF locus of *Cronobacter turicensis* comprising the nucleotide sequence of SEQ ID NO: 6, an enzyme encoded by the rpfF locus of *Enterobacter cloacae* comprising the nucleotide sequence of SEQ ID NO: 17, an enzyme encoded by the rpfF locus of *Pseudomonas aeruginosa* comprising the nucleotide sequence of SEQ ID NO: 14 or 15, an enzyme encoded by the rpfF locus of *Stenotrophomonas maltophilia* comprising the nucleotide sequence of SEQ ID NO: 11 or 12, and an enzyme encoded by the rpfF locus of *Xanthomonas campestris pathovar campestris* comprising the nucleotide sequence of SEQ ID NO: 8 or 9; or b) the enzyme comprises an amino acid sequence selected from the group consisting of SEQ ID NO: 1, SEQ ID NO: 7, SEQ ID NO 10, SEQ ID NO: 13, SEQ ID NO: 16, SEQ ID NO: 18, SEQ ID NO: 19, SEQ ID NO: 20, SEQ ID NO: 21, SEQ ID NO: 22, SEQ ID NO: 23, and SEQ ID NO: 24.

3. The genetically engineered bacterium of claim 1, wherein the enzyme is encoded by the rpfF locus of *Xylella fastidiosa* comprising the nucleotide sequence of SEQ ID NO: 2.

4. The genetically engineered bacterium of claim 1, wherein the probiotic bacterium is selected from the group consisting of *Escherichia coli* strain Nissle 1917, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*, and *Propionibacterium freudenreichii.*

5. The genetically engineered bacterium of claim 1, wherein the exogenous nucleic acid comprises a promoter.

6. The genetically engineered bacterium of claim 5, wherein the promoter is a constitutive promoter.

7. The genetically engineered bacterium of claim 5, wherein the promoter is an inducible promoter.

8. The genetically engineered bacterium of claim 1, wherein the exogenous nucleic acid is stably integrated in the bacterial genome.

9. The genetically engineered bacterium of claim 8, wherein a single copy of the exogenous nucleic acid is integrated in the bacterial genome.

10. A composition, comprising the genetically engineered bacterium according to claim 1, and a pharmaceutically or veterinarily acceptable carrier.

11. The composition of claim 10, wherein the composition is an animal feed composition.

12. A method for treating a *Salmonella* infection comprising administering to a subject in need of treatment an effective amount of the genetically engineered bacterium according to claim 1.

13. The method of claim 12, wherein:

a) the enzyme is selected from the group consisting of an enzyme encoded by the rpfF locus of *Xylella fastidiosa* comprising the nucleotide sequence of SEQ ID NOs: 2, 3, 4, or 5, an enzyme encoded by the rpfF locus of *Cronobacter turicensis* comprising the nucleotide sequence of SEQ ID NO: 6, an enzyme encoded by the rpfF locus of *Enterobacter cloacae* comprising the nucleotide sequence of SEQ ID NO: 17, an enzyme encoded by the rpfF locus of *Pseudomonas aeruginosa* comprising the nucleotide sequence of SEQ ID NO: 14 or 15, an enzyme encoded by the rpfF locus of *Stenotrophomonas maltophilia* comprising the nucleotide sequence of SEQ ID NO: 11 or 12, and an enzyme encoded by the rpfF locus of *Xanthomonas campestris pathovar campestris* comprising the nucleotide sequence of SEQ ID NO: 8 or 9; or b) the enzyme comprises an amino acid sequence selected from the group consisting of SEQ ID NO: 1, SEQ ID NO: 7, SEQ ID NO 10, SEQ ID NO: 13, SEQ ID NO: 16, SEQ ID NO: 18, SEQ ID NO: 19, SEQ ID NO: 20, SEQ ID NO: 21, SEQ ID NO: 22, SEQ ID NO: 23, and SEQ ID NO: 24.

14. The method of claim 12, wherein the enzyme is encoded by the rpfF locus of *Xylella fastidiosa* comprising the nucleotide sequence of SEQ ID NO: 2.

15. The method of claim 12, wherein the probiotic bacterium is selected from the group consisting of *Escherichia coli* strain Nissle 1917, *Lactobacillus acidophilus, Lactobacillus brevis, Lactobacillus bulgaricus, Lactobacillus casei, Lactobacillus helveticus, Lactobacillus plantarum, Lactobacillus reuteri, Lactobacillus rhamnosus, Bifidobacterium bifidum, Bifidobacterium infantis, Bifidobacterium lactis, Bifidobacterium longum, Streptococcus thermophilus*, and *Propionibacterium freudenreichii.*

16. The method of claim 12, wherein the exogenous nucleic acid comprises a promoter.

17. The method of claim 16, wherein the promoter is a constitutive promoter.

18. The method of claim 16, wherein the promoter is an inducible promoter.

19. The method of claim 12, wherein the exogenous nucleic acid is stably integrated in the bacterial genome.

20. The method of claim 19, wherein a single copy of the exogenous nucleic acid is integrated in the bacterial genome.

21. The method of claim 12, wherein the genetically engineered bacterium is within a capsule when administered.

22. The method of claim 12, wherein the subject is a human.

23. The method of claim 12, wherein the subject is a non-human animal.

24. The method of claim 23, wherein the animal is a domesticated animal.

25. A method of producing a diffusible signal factor (DSF), comprising culturing the genetically engineered bacterium of claim 1 under conditions that allow the genetically engineered bacterium to express the enzyme that produces a DSF, thereby producing the DSF.

26. The genetically engineered bacterium of claim 1, wherein the exogenous nucleic acid encodes an amino acid sequence selected from the group consisting of SEQ ID NO: 1, SEQ ID NO: 7, SEQ ID NO 10, SEQ ID NO: 13, SEQ ID NO: 16, SEQ ID NO: 18, SEQ ID NO: 19, SEQ ID NO: 20, SEQ ID NO: 21, SEQ ID NO: 22, SEQ ID NO: 23, and SEQ ID NO: 24.

27. The genetically engineered bacterium of claim 1, wherein the enzyme comprises an amino acid sequence selected from the group consisting of SEQ ID NO: 1, SEQ ID NO: 7, SEQ ID NO 10, SEQ ID NO: 13, SEQ ID NO: 16, SEQ ID NO: 18, SEQ ID NO: 19, SEQ ID NO: 20, SEQ ID NO: 21, SEQ ID NO: 22, SEQ ID NO: 23, and SEQ ID NO: 24.

* * * * *